US008993323B2

(12) United States Patent
Schoonjans

(10) Patent No.: US 8,993,323 B2
(45) Date of Patent: Mar. 31, 2015

(54) COMPOSITIONS FOR THE IN VITRO DERIVATION AND CULTURE OF EMBRYONIC STEM (ES) CELL LINES WITH GERMLINE TRANSMISSION CAPABILITY AND FOR THE CULTURE OF ADULT STEM CELLS

(71) Applicant: ThromboGenics NV, Leuven (BE)

(72) Inventor: Luc Schoonjans, Wilsele (BE)

(73) Assignee: ThromboGenics N.V., Leuven (BE)

( * ) Notice: Subject to any disclaimer, the term of this patent is extended or adjusted under 35 U.S.C. 154(b) by 0 days.

(21) Appl. No.: 14/031,592

(22) Filed: Sep. 19, 2013

(65) Prior Publication Data

US 2014/0099710 A1  Apr. 10, 2014

Related U.S. Application Data

(62) Division of application No. 12/274,939, filed on Nov. 20, 2008, now Pat. No. 8,697,444, which is a division of application No. 10/499,428, filed as application No. PCT/BE02/00196 on Dec. 20, 2002, now abandoned.

(30) Foreign Application Priority Data

Dec. 21, 2001 (WO) ........................ PCT/BE01/00221
Aug. 30, 2002 (GB) .................................. 0220145.7

(51) Int. Cl.
*C12N 5/00* (2006.01)
*C12N 5/02* (2006.01)
*C12N 5/06* (2006.01)
*C12N 5/0735* (2010.01)
*A01K 67/027* (2006.01)
*C07K 14/54* (2006.01)
*C12N 5/0789* (2010.01)
*C12N 5/078* (2010.01)
*A61K 35/12* (2006.01)

(52) U.S. Cl.
CPC ............ *C12N 5/0606* (2013.01); *C12N 5/0634* (2013.01); *C12N 2501/10* (2013.01); *C12N 2502/16* (2013.01); *A61K 35/51* (2013.01); *A01K 67/0275* (2013.01); *A01K 2217/05* (2013.01); *A61K 2035/124* (2013.01); *C07K 14/5415* (2013.01); *C12N 5/0647* (2013.01); *C12N 2501/2306* (2013.01); *C12N 2501/235* (2013.01); *C12N 2501/33* (2013.01); *C12N 2502/1323* (2013.01); *C12N 2502/99* (2013.01)
USPC ........... 435/378; 435/325; 435/372; 435/375; 435/404; 435/405

(58) Field of Classification Search
CPC .............. C12N 5/0606; C12N 5/0634; C12N 2501/10; C12N 2502/16; A61K 35/51
USPC .................. 435/325, 372, 375, 378, 404, 405
See application file for complete search history.

(56) References Cited

U.S. PATENT DOCUMENTS

| 5,166,065 | A | 11/1992 | Williams et al. |
| 5,187,077 | A | 2/1993 | Gearing et al. |
| 5,418,159 | A | 5/1995 | Gough et al. |
| 5,427,925 | A | 6/1995 | Gearing et al. |
| 5,443,825 | A | 8/1995 | Gearing et al. |
| 5,750,654 | A | 5/1998 | Gearing et al. |
| 6,261,548 | B1 | 7/2001 | Gearing et al. |
| 6,506,574 | B1 | 1/2003 | Rambhatla et al. |
| 7,297,539 | B2 | 11/2007 | Mandalam et al. |
| 2001/0024825 | A1 | 9/2001 | Thomson |
| 2004/0053406 | A1 | 3/2004 | Schoonjans et al. |
| 2005/0059145 | A1 | 3/2005 | Schoonjans |

FOREIGN PATENT DOCUMENTS

| AU | PI 1209 | 4/1987 |
| AU | PI 9644 | 8/1998 |
| EP | 0285448 | 10/1988 |
| EP | 0380646 | 2/1990 |
| JP | 10-52263 | 2/1998 |
| WO | WO 88/07548 | 10/1988 |
| WO | WO 90/01541 | 2/1990 |
| WO | WO 97/20035 | 6/1997 |
| WO | WO 01/51616 | 7/2001 |
| WO | WO 03/054169 | 7/2003 |
| WO | WO 03/054170 | 7/2003 |

OTHER PUBLICATIONS

Allegrucci et al., 2006, Human Reproduction Update, Vol. Advance Access published on Aug. 26, 2006, p. 1-18.*
Sato et al., 2003, Developmental Biology, vol. 260, p. 404-413.*
Rao, M., 2004, Developmental Biology, vol. 275, p. 269-286.*
Abeyta et al., 2004, Human Molecular Genetics, vol. 13, No. 6, p. 601-608.*
Abeyta et al., "Unique gene expression signatures of independently-derived human embryonic stem cell lines," Hum Mol Genet. 13(6):601-8 (2004).
Alenzi et al., Stem cells: biology and clinical potential,: African Journal of Biotechnology 10:19929-19940 (2011).

(Continued)

*Primary Examiner* — Shin Lin Chen
(74) *Attorney, Agent, or Firm* — Clark & Elbing LLP

(57) ABSTRACT

The present invention is directed to a method of deriving pluripotent embryonic stem cells from mouse blastocysts or from primordial germ cells from a post-implantation mouse embryo, or of maintaining or growing pluripotent embryonic stem cells from a mouse, or of expanding human hematopoietic stem cells or human hematopoietic precursor cells. The methods include the step of cultivating the stem cells or precursor cells for at least one passage in a culture medium preconditioned by the rabbit fibroblast cell line Rab9 (ATCC catalogue CRL1414) and containing less than 0.1 ng/ml Leukemia Inhibitory Factor (LIF).

12 Claims, 6 Drawing Sheets

(56) References Cited

OTHER PUBLICATIONS

Allegrucci et al., "Differences between human embryonic stem cell lines," Human Reproduction. 1-18 (2006).
Fehrer et al., "Mesenchymal stem cell aging," Experimental Gerontology 40:926-930 (2005).
Kolf et al., "Biology of adult mesenchymal stem cells: regulation of niche, self-renewal and differentiation," Arthritis Research & Therapy 9:204 (10 pages) (2007).
Nguyen et al., "Methods to assess stem cell lineage, fate and function," Advanced Drug Delivery Reviews 62:1175-1186 (2010).
Sato et al., "Molecular signature of human embryonic stem cells and its comparison with the mouse," Dev Biol. 260(2):404-13 (2003).
Sun et al., "Mechanisms controlling embryonic stem cell self-renewal and differentiation," Critical Reviews in Eukaryotic Gene Expression 16:211-231 (2006).
Xu et al., "Feeder-free growth of undifferentiated human embryonic stem cells," Nat Biotechnol. 19:971-4 (2001).
Takahama et al., "Molecular Cloning and Functional Analysis of cDNA Encoding a Rat Leukemia Inhibitory Factor: Towards Generation of Pluripotent Rat Embryonic Stem Cells," Oncogene 16(24):3189-3196 (1998).
Office Action for Japanese Patent Application No. 554874/2003, mailed Jul. 7, 2009.
English language translation of Office Action for Japanese Application No. 554874/2003, mailed Jul. 7, 2009.
Hearing Notice issued in Indian Application No. 1761/DELNP/2004, on Feb. 22, 2012.
Amano et al., "Comparison of Heat-Treated and Tetraploid Blastocysts for the Production of Completely ES-Cell-Derived Mice," Zygote 9:153-7 (2001).
Carney et al., "Co-Culture of Rabbit 2-Cell Embryos with Rabbit Oviduct Epithelial Cells and other Somatic Cells," Mol. Reprod. Dev. 27(3):209-215 (1990).
de Angelis et al., "Promotion of Gastrulation by Maternal Growth Factor in Cultured Rabbit Blastocysts," Cell Tissue Res. 282:147-154 (1995).
de Wynter et al., "Assays for the Assessment of Human Hematopoietic Stem Cells," J. Biol. Regul. Homeost. Agents 15:23-7 (2001).
Dupont, "Immunology of Hematopoietic Stem Cell Transplantation: A Brief Review of its History," Immunol. Rev. 157: 5-12 (1997).
Eggan et al., "Hybrid Vigor, Fetal Overgrowth, and Viability of Mice Derived by Nuclear Cloning and Tetraploid Embryo Complementation," Proc. Natl. Acad. Sci. USA 98(11):6209-14 (2001).
Fasouliotis et al., "Human Umbilical Cord Blood Banking and Transplantation: A State of the Art," Eur. J. Obstet. Gynecol. Reprod. Biol. 90:13-25 (2000).
Gardner et al., "Reflections on the Biology of Embryonic Stem (ES) Cells", Int. J. Dev. Biol., 41:235-243 (1997).
Gluckman et al., "Hematopoietic Reconstitution in a Patient with Fanconi's Anemia by Means of Umbilical-Cord Blood from an HLA-Identical Sibling," N. Engl. J. Med. 321(17):1174-8 (1989).
Graves et al., "Derivation and Characterization of Putative Pluripotential Embryonic Stem Cells from Preimplantation Rabbit Embryos," Mol. Reprod. Dev. 36:424-33 (1993).
Henon et al., "Importance of $CD34^+$ Cell Subsets in Autologous PBSC Transplantation: The Mulhouse Experience Using $CD34^+CD38^-$ Cells as Predictive Tool for Hematopoietic Engraftment," J. Bio. Regul. Homeost. Agents 15:62-7 (2001).
Lagasse et al., "Toward Regenerative Medicine," Immunity 14:425-36 (2001).
Lewis et al., "Umbilical Cord Blood Cells Capable of Engrafting in Primary, Secondary, and Tertiary Xenogeneic Hosts are Preserved After Ex Vivo Culture in a Noncontact System," Blood 97(11):3441-9 (2001).
Lowe et al., "Genomic Cloning and Heterologous Expression of Human Differentiation-Stimulating Factor," DNA 8(5):351-9 (1989).
Mayani et al., "Biology of Human Umbilical Cord Blood-Derived Hematopoietic Stem/Progenitor Cells," Stem Cells 16:153-65 (1998).
McWhir et al., "Selective Ablation of Differentiated Cells Permits Isolation of Embryonic Stem Cell Lines from Murine Embryos with a Non-permissive Genetic Background", Nature Genetics, 14:223-226 (1996).
Nagy et al., "Derivation of Completely Cell Culture-Derived Mice from Early-Passage Embryonic Stem Cells," Proc. Natl. Acad. Sci. USA 90:8424-8 (1993).
Pease et al., "Isolation of Embryonic Stem (ES) Cells in Media Supplemented with Recombinant Leukemia Inhibitory Factor (LIF)", Developmental Biology, 141:344-352 (1990).
Piacibello et al., "Extensive Amplification and Self-Renewal of Human Primitive Hematopoietic Stem Cells From Cord Blood," Blood 89(8):2644-53 (1997).
Piacibello et al., "Engraftments in Nonobese Diabetic Severe Combined Immunodeficient Mice of Human $CD34^+$ Cord Blood Cells After Ex Vivo Expansion: Evidence for the Amplification and Self-Renewal of Repopulating Stem Cells," Blood 93(11):3736-49 (1999).
Sirchia et al., "Placental/Umbilical Cord Blood Transplantation," Haematologica 84:738-47 (1999).
Smith et al., "Inhibition of Pluripotential Embryonic Stem Cell Differentiation by Purified Polypeptides," Nature 336:688-90 (1988).
Smith et al., "Differentiation Inhibiting Activity (DIA/LIF) and Mouse Development," Dev. Biol. 151:339-51 (1992).
Stahl et al., Accession No. M63419 (1990).
Stahl et al., Accession No. M63420 (1990).
Tomida et al., "Purification of a Factor Inducing Differentiation of Mouse Myeloid Leukemic M1 Cells from Conditioned Medium or Mouse Fibroblast L929 Cells," J. Biol. Chem. 259(17):10978-82 (1984).
Wernette-Hammond et al., "Beta-Very Low Density Lipoprotein Uptake in Cultured Fibroblasts and Smooth Muscle Cells from Watanabe Heritable Hyperlipidemic Rabbits," Arteriosclerosis, Thrombosis, and Vascular Biology, 9: 501-510, 1989.
Verfaillie, "Hematopoietic Stem Cells for Transplantation," Nature Immunol. 3(4):314-7 (2002).
Xu et al., "Feeder-Free Growth of Undifferentiated Human Embryonic Stem Cells," Nat. Biotechnol. 19(10):971-974 (2001).
European Communication, Appl. No. 02 805 233.0-2405 (mailed Mar. 8, 2007).

* cited by examiner

```
                10              20              30              40
ATG AAG ATC TTG GCG GCA GGA GTC GTG CCC CTG CTG CTG GTC TTG CAC
 M   K   I   L   A   A   G   V   V   P   L   L   L   V   L   H>

50              60              70              80              90
TGG AAA CCC GGG GCG GGG AGC CCC CTT CCC ATC AAC CCC GTC AAC GCC
 W   K   P   G   A   G   S   P   L   P   I   N   P   V   N   A>

100             110             120             130             140
ACC TGC AAC ACA CAC CAC CCA TGC CCC AGC AAC CTC ATG AGC CAG ATC
 T   C   N   T   H   H   P   C   P   S   N   L   M   S   Q   I>

150             160             170             180             190
AGG AGC CAG CTG GCA CAG CTC AAT GGC ACT GCC AAC GCC CTC TTT ATT
 R   S   Q   L   A   Q   L   N   G   T   A   N   A   L   F   I>

200             210             220             230             240
CTC TAT TAC ACA GCC CAA GGG GAG CCG TTC CCC AAC AAC CTG GAC AAG
 L   Y   Y   T   A   Q   G   E   P   F   P   N   N   L   D   K>

250             260             270             280
CTG TGC GGC CCC AAT GTG ACG GAC TTC CCG CCC TTC CAC GCC AAC GGC
 L   C   G   P   N   V   T   D   F   P   P   F   H   A   N   G>

290             300             310             320             330
ACG GAG AAG GTC AGG CTG GTG GAG CTG TAC CGC ATC GTC GCC TAC CTT
 T   E   K   V   R   L   V   E   L   Y   R   I   V   A   Y   L>

340             350             360             370             380
GGC ACC GCC CTG GGC AAC ATC ACC CGG GAC CAG AAG ACC CTC AAC CCC
 G   T   A   L   G   N   I   T   R   D   Q   K   T   L   N   P>

390             400             410             420             430
ACG GCG CAC AGC CTG CAC AGC AAA CTC AAC GCC ACG GCG GAC ACG CTG
 T   A   H   S   L   H   S   K   L   N   A   T   A   D   T   L>

440             450             460             470             480
CGG GGC CTG CTT AGC AAC GTG CTG TGC CGC CTG TGC AGC AAG TAC CAC
 R   G   L   L   S   N   V   L   C   R   L   C   S   K   Y   H>

490             500             510             520
GTG GCC CAC GTG GAC GTG GCC TAT GGC CCG GAC ACC TCG GGC AAG GAC
 V   A   H   V   D   V   A   Y   G   P   D   T   S   G   K   D>

530             540             550             560             570
GTC TTC CAG AAG AAG AAG CTG GGG TGT CAG CTG CTG GGA AAA TAC AAG
 V   F   Q   K   K   K   L   G   C   Q   L   L   G   K   Y   K>

580             590             600
CAG GTC ATG GCC GTG TTG GCG CAG GCC TTC TAG
 Q   V   M   A   V   L   A   Q   A   F   *>
```

Figure 1

```
        10              20              30              40
GCT CCA CTT CCA ATC AAC CCA GTT AAC GCT ACC TGC AAC ACA CAC CAC
 A   P   L   P   I   N   P   V   N   A   T   C   N   T   H   H>

50              60              70              80              90
CCA TGC CCA TCC AAC TTG ATG AGC CAG ATC CGT TCC CAG CTA GCA CAG
 P   C   P   S   N   L   M   S   Q   I   R   S   Q   L   A   Q>

100             110             120             130             140
TTG AAT GGC ACT GCC AAC GCC TTG TTC ATC TTG TAC TAC ACA GCC CAA
 L   N   G   T   A   N   A   L   F   I   L   Y   Y   T   A   Q>

150             160             170             180             190
GGT GAG CCA TTC CCA AAC AAC CTG GAC AAG CTG TGC GGC CCA AAT GTT
 G   E   P   F   P   N   N   L   D   K   L   C   G   P   N   V>

200             210             220             230             240
ACG GAC TTC CCA CCA TTC CAC GCT AAC GGT ACC GAG AAG GTT AGA CTA
 T   D   F   P   P   F   H   A   N   G   T   E   K   V   R   L>

250             260             270             280
GTT GAG TTG TAC CGT ATC GTG GCT TAC CTA GGC ACC GCT CTG GGC AAC
 V   E   L   Y   R   I   V   A   Y   L   G   T   A   L   G   N>

290             300             310             320             330
ATC ACC CGT GAC CAG AAG ACC CTA AAC CCA ACG GCT CAC AGC TTG CAC
 I   T   R   D   Q   K   T   L   N   P   T   A   H   S   L   H>

340             350             360             370             380
AGC AAA CTA AAC GCC ACC GCG GAC ACG TTG CGT GGC CTG CTT AGC AAC
 S   K   L   N   A   T   A   D   T   L   R   G   L   L   S   N>

390             400             410             420             430
GTG CTG TGC CGC CTG TGC AGC AAG TAC CAC GTG GCC CAC GTG GAC GTG
 V   L   C   R   L   C   S   K   Y   H   V   A   H   V   D   V>

440             450             460             470             480
GCA TAT GGC CCA GAC ACC TCT GGC AAG GAC GTT TTC CAG AAG AAG AAG
 A   Y   G   P   D   T   S   G   K   D   V   F   Q   K   K   K>

490             500             510             520
TTG GGT TGT CAG TTG TTG GGT AAA TAC AAG CAG GTC ATG GCC GTG TTG
 L   G   C   Q   L   L   G   K   Y   K   Q   V   M   A   V   L>

530             540
GCT CAG GCC TTC TAG
 A   Q   A   F   *>
```

Figure 2

SEQUENCE LISTING

```
<160> NUMBER OF SEQ ID NOS: 4

<210> SEQ ID NO 1
<211> LENGTH: 609
<212> TYPE: DNA
<213> ORGANISM: Oryctolagus cuniculus
<220> FEATURE:
<221> NAME/KEY: CDS
<222> LOCATION: (1)..(609)

<400> SEQUENCE: 1 atg aag atc ttg gcg gca gga gtc gtg ccc ctg ctg ctg gtc ttg cac      48
Met Lys Ile Leu Ala Ala Gly Val Val Pro Leu Leu Leu Val Leu His
1               5                   10                  15 tgg aaa ccc ggg gcg ggg agc ccc ctt ccc atc aac ccc gtc aac gcc      96
Trp Lys Pro Gly Ala Gly Ser Pro Leu Pro Ile Asn Pro Val Asn Ala
            20                  25                  30 acc tgc aac aca cac cac cca tgc ccc agc aac ctc atg agc cag atc     144
Thr Cys Asn Thr His His Pro Cys Pro Ser Asn Leu Met Ser Gln Ile
        35                  40                  45 agg agc cag ctg gca cag ctc aat ggc act gcc aac gcc ctc ttt att     192
Arg Ser Gln Leu Ala Gln Leu Asn Gly Thr Ala Asn Ala Leu Phe Ile
    50                  55                  60 ctc tat tac aca gcc caa ggg gag ccg ttc ccc aac aac ctg gac aag     240
Leu Tyr Tyr Thr Ala Gln Gly Glu Pro Phe Pro Asn Asn Leu Asp Lys
65                  70                  75                  80 ctg tgc ggc ccc aat gtg acg gac ttc ccg ccc ttc cac gcc aac ggc     288
```

```
                  Leu Cys Gly Pro Asn Val Thr Asp Phe Pro Phe His Ala Asn Gly
                                   85                  90                  95 acg gag aag gtc agg ctg gtg gag ctg tac cgc atc gtc gcc tac ctt      336
Thr Glu Lys Val Arg Leu Val Glu Leu Tyr Arg Ile Val Ala Tyr Leu
                100                 105                 110 ggc acc gcc ctg ggc aac atc acc cgg gac cag aag acc ctc aac ccc      384
Gly Thr Ala Leu Gly Asn Ile Thr Arg Asp Gln Lys Thr Leu Asn Pro
            115                 120                 125 acg gcg cac agc ctg cac agc aaa ctc aac gcc acg gcg gac acg ctg      432
Thr Ala His Ser Leu His Ser Lys Leu Asn Ala Thr Ala Asp Thr Leu
        130                 135                 140 cgg ggc ctg ctt agc aac gtg ctg tgc cgc ctg tgc agc aag tac cac      480
Arg Gly Leu Leu Ser Asn Val Leu Cys Arg Leu Cys Ser Lys Tyr His
145                 150                 155                 160 gtg gcc cac gtg gac gtg gcc tat ggc ccg gac acc tcg ggc aag gac      528
Val Ala His Val Asp Val Ala Tyr Gly Pro Asp Thr Ser Gly Lys Asp
                165                 170                 175 gtc ttc cag aag aag aag ctg ggg tgt cag ctg ctg gga aaa tac aag      576
Val Phe Gln Lys Lys Lys Leu Gly Cys Gln Leu Leu Gly Lys Tyr Lys
            180                 185                 190 cag gtc atg gcc gtg ttg gcg cag gcc ttc tag                          609
Gln Val Met Ala Val Leu Ala Gln Ala Phe
        195                 200

<210> SEQ ID NO 2
<211> LENGTH: 202
<212> TYPE: PRT
<213> ORGANISM: Oryctolagus cuniculus

<400> SEQUENCE: 2

Met Lys Ile Leu Ala Ala Gly Val Val Pro Leu Leu Leu Val Leu His
1               5                   10                  15

Trp Lys Pro Gly Ala Gly Ser Pro Leu Pro Ile Asn Pro Val Asn Ala
                20                  25                  30

Thr Cys Asn Thr His His Pro Cys Pro Ser Asn Leu Met Ser Gln Ile
            35                  40                  45

Arg Ser Gln Leu Ala Gln Leu Asn Gly Thr Ala Asn Ala Leu Phe Ile
50                  55                  60

Leu Tyr Tyr Thr Ala Gln Gly Glu Pro Phe Pro Asn Asn Leu Asp Lys
65                  70                  75                  80

Leu Cys Gly Pro Asn Val Thr Asp Phe Pro Phe His Ala Asn Gly
                85                  90                  95

Thr Glu Lys Val Arg Leu Val Glu Leu Tyr Arg Ile Val Ala Tyr Leu
                100                 105                 110

Gly Thr Ala Leu Gly Asn Ile Thr Arg Asp Gln Lys Thr Leu Asn Pro
            115                 120                 125

Thr Ala His Ser Leu His Ser Lys Leu Asn Ala Thr Ala Asp Thr Leu
        130                 135                 140

Arg Gly Leu Leu Ser Asn Val Leu Cys Arg Leu Cys Ser Lys Tyr His
145                 150                 155                 160

Val Ala His Val Asp Val Ala Tyr Gly Pro Asp Thr Ser Gly Lys Asp
                165                 170                 175

Val Phe Gln Lys Lys Lys Leu Gly Cys Gln Leu Leu Gly Lys Tyr Lys
            180                 185                 190

Gln Val Met Ala Val Leu Ala Gln Ala Phe
        195                 200
```

-continued

```
<210> SEQ ID NO 3
<211> LENGTH: 543
<212> TYPE: DNA
<213> ORGANISM: Oryctolagus cuniculus
<220> FEATURE:
<221> NAME/KEY: CDS
<222> LOCATION: (1)..(543)

<400> SEQUENCE: 3 gct cca ctt cca atc aac cca gtt aac gct acc tgc aac aca cac cac      48
Ala Pro Leu Pro Ile Asn Pro Val Asn Ala Thr Cys Asn Thr His His
1               5                   10                  15 cca tgc cca tcc aac ttg atg agc cag atc cgt tcc cag cta gca cag      96
Pro Cys Pro Ser Asn Leu Met Ser Gln Ile Arg Ser Gln Leu Ala Gln
            20                  25                  30 ttg aat ggc act gcc aac gcc ttg ttc atc ttg tac tac aca gcc caa     144
Leu Asn Gly Thr Ala Asn Ala Leu Phe Ile Leu Tyr Tyr Thr Ala Gln
        35                  40                  45 ggt gag cca ttc cca aac aac ctg gac aag ctg tgc ggc cca aat gtt     192
Gly Glu Pro Phe Pro Asn Asn Leu Asp Lys Leu Cys Gly Pro Asn Val
    50                  55                  60 acg gac ttc cca cca ttc cac gct aac ggt acc gag aag gtt aga cta     240
Thr Asp Phe Pro Pro Phe His Ala Asn Gly Thr Glu Lys Val Arg Leu
65                  70                  75                  80 gtt gag ttg tac cgt atc gtg gct tac cta ggc acc gct ctg ggc aac     288
Val Glu Leu Tyr Arg Ile Val Ala Tyr Leu Gly Thr Ala Leu Gly Asn
                85                  90                  95 atc acc cgt gac cag aag acc cta aac cca acg gct cac agc ttg cac     336
Ile Thr Arg Asp Gln Lys Thr Leu Asn Pro Thr Ala His Ser Leu His
            100                 105                 110 agc aaa cta aac gcc acc gcg gac acg ttg cgt ggc ctg ctt agc aac     384
Ser Lys Leu Asn Ala Thr Ala Asp Thr Leu Arg Gly Leu Leu Ser Asn
        115                 120                 125 gtg ctg tgc cgc ctg tgc agc aag tac cac gtg gcc cac gtg gac gtg     432
Val Leu Cys Arg Leu Cys Ser Lys Tyr His Val Ala His Val Asp Val
    130                 135                 140 gca tat ggc cca gac acc tct ggc aag gac gtt ttc cag aag aag aag     480
Ala Tyr Gly Pro Asp Thr Ser Gly Lys Asp Val Phe Gln Lys Lys Lys
145                 150                 155                 160 ttg ggt tgt cag ttg ttg ggt aaa tac aag cag gtc atg gcc gtg ttg     528
Leu Gly Cys Gln Leu Leu Gly Lys Tyr Lys Gln Val Met Ala Val Leu
                165                 170                 175 gct cag gcc ttc tag                                                  543
Ala Gln Ala Phe
            180

<210> SEQ ID NO 4
<211> LENGTH: 180
<212> TYPE: PRT
<213> ORGANISM: Oryctolagus cuniculus

<400> SEQUENCE: 4

Ala Pro Leu Pro Ile Asn Pro Val Asn Ala Thr Cys Asn Thr His His
1               5                   10                  15

Pro Cys Pro Ser Asn Leu Met Ser Gln Ile Arg Ser Gln Leu Ala Gln
            20                  25                  30

Leu Asn Gly Thr Ala Asn Ala Leu Phe Ile Leu Tyr Tyr Thr Ala Gln
        35                  40                  45

Gly Glu Pro Phe Pro Asn Asn Leu Asp Lys Leu Cys Gly Pro Asn Val
    50                  55                  60

Thr Asp Phe Pro Pro Phe His Ala Asn Gly Thr Glu Lys Val Arg Leu
```

-continued

```
65                  70                  75                  80
Val Glu Leu Tyr Arg Ile Val Ala Tyr Leu Gly Thr Ala Leu Gly Asn
                85                  90                  95

Ile Thr Arg Asp Gln Lys Thr Leu Asn Pro Thr Ala His Ser Leu His
                100                 105                 110

Ser Lys Leu Asn Ala Thr Ala Asp Thr Leu Arg Gly Leu Leu Ser Asn
            115                 120                 125

Val Leu Cys Arg Leu Cys Ser Lys Tyr His Val Ala His Val Asp Val
            130                 135                 140

Ala Tyr Gly Pro Asp Thr Ser Gly Lys Asp Val Phe Gln Lys Lys Lys
145                 150                 155                 160

Leu Gly Cys Gln Leu Leu Gly Lys Tyr Lys Gln Val Met Ala Val Leu
                165                 170                 175

Ala Gln Ala Phe
            180
```

COMPOSITIONS FOR THE IN VITRO DERIVATION AND CULTURE OF EMBRYONIC STEM (ES) CELL LINES WITH GERMLINE TRANSMISSION CAPABILITY AND FOR THE CULTURE OF ADULT STEM CELLS

FIELD OF THE INVENTION

The present invention relates to novel compositions and their use for the derivation, maintenance and growth of pluripotent and germline competent embryonic stem (ES) cells. The invention also relates to the ES cells produced using the composition and to use of these ES cell lines for germline transmission and for the generation of genetically modified non-human animals. The present invention further relates to novel compositions and their use for the derivation, maintenance and growth of adult stem cells (ASC).

BACKGROUND OF THE INVENTION

Embryonic Stem Cells

ES cell lines are cell lines isolated from the inner cell mass (ICM) of blastocyst-stage embryos, which under specific conditions can be maintained in culture for many passages, i.e. replating of cells onto new cell culture dishes at regular time intervals, without loss of their pluripotency. They maintain a normal karyotype and when reintroduced into a host blastocyst they can colonize the germline. Such cell lines may provide an abundance of pluripotent cells that can be transformed in vitro with DNA (see below), and selected for recombination (homologous or non-homologous) of exogenous DNA into chromosomal DNA, allowing stable incorporation of the desired gene. To date, germline transmission, i.e. the transmission of the ES genome to the next generation, has however only been achieved with ES cells of certain mouse strains.

Murine embryonic stem cells were first isolated in 1981. Since then, several ES cell lines have been established and they are now widely and successfully used for the introduction of targeted mutations or other genetic alterations into the mouse genome. Most of the germline-competent mouse ES cell lines that are in current use have been obtained in the 129 strain, and the remainder in a few other inbred strains (C57BL/6 and crosses with C57BL/6). Furthermore, ES cell lines are at best obtained in 30% of explanted blastocysts, even in the 129 strain, and success rates of around 10% appear to be closer to the norm.

The most commonly used approach to generate chimeric animals is to inject about 10-15 isolated ES cells into the blastocoel of a host blastocyst and to allow the cells to mix with the cells of the inner cell mass. The resultant chimeric blastocysts are then transferred to recipients for rearing. Alternatively diploid aggregation using very early (8-16 cell) stage embryos and tetraploid aggregation, can be used as hosts for ES cells. Briefly, ES cells are 'sandwiched' between early stage embryos devoid of their zona pellucida, cultured overnight and implanted into a foster mother. This technique can be performed under conditions yielding either chimeric or totally ES cell-derived offspring.

Although ES cell culture and chimera production have been technically improved over the years, the pluripotency of the ES cells is still often reduced after several passages, whereas completely ES cell-derived fetuses (by tetraploid aggregation) seem to have a markedly reduced survival after birth. Nagy et al., "Derivation of completely cell culture derived mice from early-passage embryonic stem cells" Proc Natl Acad Sci USA 1993; 90: 8424-8, used R1 ES cell lines derived from early passages with electrofusion derived tetraploid embryos to form aggregates and obtained mice which were entirely derived from ES cells. However, the R1 ES cells lost their totipotency upon extended culture in vitro, because no animal survived to adulthood from ES cells obtained from later than 14 passages. Moreover, even when early passage cells were used, many ES-tetraploid aggregates died before developing to term. Only 3.8% of transferred aggregates survived after caesarian section. The goal to obtain viable ES mice using later passage ES cells was not reached and the production of ES cell derived mice using genetically modified ES cells did not seem to be possible.

The inability of the present technology to yield viable offspring from ES cells of inbred mouse strains via tetraploid aggregation was recently confirmed in Eggan K, et al. "Hybrid vigor, fetal overgrowth, and viability of mice derived by nuclear cloning and tetraploid embryo complementation. Proc Natl Acad Sci 2001; 98: 6209-14. Genetic heterozygosity was found to be a crucial parameter influencing postnatal survival of offspring derived from ES cells by nuclear cloning or tetraploid embryo complementation. Pups derived from inbred ES cells by either method died perinatally with a phenotype of respiratory failure. In contrast, the great majority (80-85%) of pups derived from F1 ES cells by either procedure survived to adulthood. In another study however, no clear correlation was found between the postnatal lethality of ES-cell-derived mice and the cell line used. Postnatal death occurred in all cell lines, including those with different genetic background. Thirty four completely ES-cell-derived newborns (3%) were obtained after transfer of 1037 tetraploid blastocysts injected with ES from all cell lines. Only thirteen mice (1%) grew to adulthood (Amano T, Kato Y, Tsunoda Y. Comparison of heat-treated and tetraploid blastocysts for the production of completely ES-cell-derived mice. Zygote 2001; 9: 153-7).

Presumptive pluripotential ES cells have been isolated from a number of other species than mice, including hamster, pig, sheep, cattle, mink, rat, primate, human, chicken, marmoset, medakafish and man. In only a few instances (pig, chicken, medakafish), have these cell lines given rise to chimeras when reintroduced into blastocysts, but thus far none have given rise to germline transmission.

The isolation of pluripotential ES cell lines from preimplantation rabbit blastocysts was reported by Graves K H, Moreadith R W, "Derivation and characterization of putative pluripotential embryonic stem cells from preimplantation rabbit embryos", Mol Reprod Dev 1993; 36: 424-33. These ES lines were found to give rise to differentiated cell types, representative of all three germ layers (pluripotential by in vitro criteria). Recently these ES lines from the Dutch Belted strain were shown to be also capable of generating overt coat-color chimeras following injection into recipient New Zealand White blastocysts, demonstrating that the cells were pluripotential by in vivo criteria as well. However no germline transmission has been achieved. Additional experiments showed that the low frequency of chimera formation and absence of germline transmission probably was due to the loss of pluripotency of the ES cell line upon high passage number.

ES cells are maintained in an undifferentiated state by the presence of feeder layers producing various factor(s) that prevent the cells from differentiating. It has been shown that several cytokines are responsible for this effect: DIA/LIF (differentiation inhibitory activity/leukaemia inhibiting factor), interleukin-6 in combination with soluble interleukin-6 receptor, interleukin-11, oncostatin M, ciliary neurotrophic factor and cardiotrophin. It is now possible to establish and maintain ES cells in culture in the absence of feeder cells but in the presence of such factors, at least for several passages. In species other than the mouse, ES cell technology is still under development and there are no published data reporting germ line transmission in any species other than mouse.

Recombinant Leukemia Inhibitory Factor (LIF) is presently routinely added to the culture medium used for the isolation of embryonic stem (ES) cells from mammalian embryos in vitro. This method is claimed in U.S. Pat. No. 5,166,065, EP 0380646 and WO9001541, based on a priority document AU1988 PI09644 dated Aug. 4, 1988 (51-53). Recombinant murine or human LIF protein was purified and cDNA cloned on the basis of its ability to induce differentiation of the murine monocytic cell line M1 in mature macrophages with consequent reduced clonogenicity. The (recombinant) protein and cDNA's (the murine and human variants) are claimed in a.o. U.S. Pat. No. 5,187,077 (and several continuations in part to up to U.S. Pat. No. 6,261,548 issued 17 Jul. 2001) and EP 285448, based on a priority document of AU1987 PI1209 dated Apr. 2, 1987.

Subsequent work has established the identity of LIF with earlier purified proteins and/or biological activities. The work of Hozumi et al. during 1980-1986 led to the purification to homogeneity of Factor D which stimulated the differentiation and inhibited the proliferation of the murine monocytic cell line M1, Tomida M, Yamamoto-Yamaguchi Y, Hozumi M. Purification of a factor inducing differentiation of mouse myeloid leukemic M1 cells from conditioned medium or mouse fibroblast L929 cells. J Biol Chem 1984; 259: 10978-82). The Factor D cDNA was subsequently shown to be identical to that of LIF (Lowe D G, Nunes W, Bombara M, McCabe S, Ranges G E, Henzel W, Tomida M, Yamamoto-Yamaguchi Y, Hozumi M, Goeddel D V. Genomic cloning and heterologous expression of human differentiation-stimulating factor. DNA 1989; 8: 351-9). The use of LIF in the culture medium of ES cells was preceded by work on the inhibition of the differentiation of murine embryonic stem cells by DIA (differentiation inhibiting activity) secreted by Buffalo rat liver cells. Subsequently the identity of DIA and LIF was established at the cDNA and protein level (Smith A G, Heath J K, Donaldson D D, Wong G C, Moreau J, Stahl M, Rogers D. Inhibition of pluripotential embryonic stem cell differentiation by purified polypeptides. Nature 1988; 336: 688-90; Smith A G, Nichols J, Robertson M, Rathjen P D. Differentiation inhibiting activity (DIA/LIF) and mouse development. Devel Biol 1992; 151: 339-51.).

Advances in recombinant DNA technology over the last decade have greatly facilitated the isolation and manipulation of genes, to the point where any conceivable novel construct can be engineered, such as by fusing the promoter of one gene to the coding sequence of another, or by site-directed mutagenesis. Likewise, advances in embryo manipulation have facilitated the transfer of these novel exogenous genes into endogenous chromosomal DNA, generating transgenic animals. Transgenic animals can be generated either by injection of DNA into the pronucleus of zygotes, by introduction of (genetically manipulated) pluripotent embryonic stem (ES) cells into host "embryos", and more recently by nuclear transfer with stably transfected somatic donor cells into enucleated oocytes.

The review of the current technology shows that there is a need for economic compositions that provide ES cells which remain pluripotent and germ line competent after prolonged passaging. There is also a need for the generation of transgenic mice of strains with different genetic background and for the generation of other non human transgenic mammals. These transgenic animals could be useful for the study of the biological effects of identified genes, for the pharmaceutical production of therapeutic gene products, for the generation of "improved" live stock, etc.

The difficulties in maintaining the undifferentiated phenotype of cultivated stem cells is not limited to embryonic stem cells. Also adult stem cells of different lineages tend to loose their capacity to differentiate in different cell types. The maintenance of the stem cell phenotype is especially challenging for hematopoietic stem cells.

A hematopoietic stem cell (abbreviated as HSC) is a cell isolated from peripheral blood, umbilical cord blood or bone marrow that can renew itself, can differentiate to a variety of specialized cells. The bone marrow HSC can mobilize out of the bone marrow. HSC can undergo programmed cell death, called apoptosis—a process by which cells that are detrimental or unneeded self-destruct. About 1 in every 10,000 to 15,000 bone marrow cells is thought to be a stem cell. In the blood stream the proportion falls to 1 in 100,000 blood cells. (Stem cells: scientific progress and future research directions June 2001, NIH)

During the last 30 years, transplantation of hematopoietic progenitor/stem cells from bone marrow and mobilized peripheral blood is a procedure of unquestioned clinical utility and a standard of care in a number of malignancies, benign and dysplastic hematologic disorders and inherited diseases (Dupont B. (1997) in Immunology Reviews, Vol. 157, 5-12.)

Hematopoietic transplants are especially successful in treatments involving high dose chemotherapy or radiation aiming to destroy existing diseased blood cells or tumors, thereby limiting the blood, stroma and immune patients' ability to regenerate cells of the blood and immune system. The donated stem cells are infused into a patient's vein and if the transplant is successful, the donated hematopoietic stem cells will grow in number and restore the recipient's marrow and its blood-forming function.

Despite expanding roles for autologous bone marrow or peripheral blood stem cells, many indications require allogeneic transplantation, due to the potential risk of transferring malignant cells with the transplant in patients with malignant disease after autologous stem cell transplantation, and also, because the number of available human leukocyte antigen (HLA)-identical siblings is often limited. The principal limitations of allogeneic bone marrow transplantation are the lack of suitable fully HLA-matched donors and the complications of graft-versus-host disease associated with HLA-disparities.

The finding that placenta blood, also known as umbilical cord blood (UCB) contains high numbers of HSC, a comparable frequency of myeloid and erythroid progenitors to adult bone marrow, a higher proportion of immature colony-forming cells, a decreased risk of transmission of infection and higher percentage of telomerase, promises to circumvent many of the problems (Mayani H, Lansdorp P. in (1998) Stem Cells. 16, 153-165). The success of the first transplant performed in 1988 in a Fanconi's anemia patient (Gluckman E. et al (1989) in N. Engl. J. Med., 321: 1174-8) has proven that human UCB is a feasible alternative source of HSCs and prompted the development of large worldwide Cord Blood banking programs (Sirchia G. and Rebulla P. (1999) in Haematologica, 84: 738-747)

The most important disadvantage of umbilical cord blood is that average donations contain only $1.5\ 10^9$ nucleated cells as average, one tenth of the nucleated cell (NC) dose conventionally used for bone marrow transplants in adults (Fasouliotis S, and Schenker J. (1999). Eur. J. Obst. Gynecol. Reprod. Biol. 9: 13-25). Doctors are rarely able to extract more than a few million UCB HSCs, too few to use in a transplant for an adult, who would ideally get 7 to 10 million CD34+ cells per kilogram body weight (b.w.) but often adequate for a transplant for a child even though a frequent discrepancy still exists between the number of CD34+ cells reinfused and the engraftment efficiency. Recently some authors proposed a threshold dose of $5 \times 10^4$ CD34+CD38− cells/kg b.w. below which the trilineage engraftment kinetics are significantly slower and unpredictable (Henon P H et al. (2001) in J. Biol. Regul. Homeost. Agents. 15, 62-67). This lower NC number implies potential limitations for the widespread use of the cord blood. Therefore a major challenge in stem cell research is the development of ex vivo culture conditions that facilitate in vitro maintenance and expansion of long term transplantable HSCs. Establishment of such culture systems is a prerequisite for potential ex vivo manipulation and expansion of transplantable HSCs in several clinical applications such as gene therapy, tumor cell purging, and stem cell transplantation.

There is a need for suitable laboratory conditions wherein stem cells can be stimulated to expand without losing their stem cell properties, thus increasing the dose of transplantable cells derived from a single donor to a transplant patient. Expansion of HSCs has proven problematic and scientists face major roadblocks in expanding their use beyond the replacement of blood and immune system. First, HSCs are unable to proliferate (replicate themselves) and differentiate (become specialized to other cell types) in vitro (Lagasse E., Weissman I L., (2001) in Immunity, 14, 425-436.). Secondly scientists do not have yet an accurate idea of the identity of a true stem cell. Although the ex vivo expansion of long term repopulating cells under stroma free conditions has not yet been achieved in a reproducible way, it is suggested that the continued quest for mechanisms that govern the proliferation and differentiation of hematopoietic stem cells could lead to the development of culture systems that expand not only committed progenitors but also HSCs (Verfaillie C. (2002). in Nature Immunol. 3, 314-317). Lewis I. et al (2001) in Blood 97, 3441-3449, present the expansion of HUC derived CD34+ cells in non-contact cultures with feeder cells with a combination of cytokines and show that these expanded cells can repopulate engrafted NOD/SCID (Non Obese Diabetic/Severe Combined Immunodeficient) mice. Piacibello et al (1997) in Blood 89, 2644-2653 show that CD34+ HUC derived cells rapidly decrease in number and die within three weeks in cultures without added cytokines. Piacibello et al (1999) in Blood 93, 11, 3736-3749 describe that CD341 HUC cells can be expanded for up to 10 weeks in stroma-free cultures in the presence of a cocktail of growth factors without losing their in vivo repopulating potential as assayed by the repopulation of sublethally irradiated NOD/SCID mice. There is thus still a need for novel or alternative media with or without added growth factors for the expansion of adult stem cells and early progenitor cells such as HSC.

SUMMARY OF THE INVENTION

The present invention is directed to novel and superior compositions for deriving, maintaining and growing pluripotent and germline competent mammalian embryonic stem cells and the use of these compositions.

In a first aspect of the invention, the composition for deriving, maintaining and growing pluripotent and germline competent human or non-human mammalian embryonic stem cells is provided comprising a conditioned medium from certain cells and wherein the composition contains less than 2 ng/ml of leukemia inhibitory factor (LIF) as assayed by an immunoassay, e.g. an ELISA using antibodies which cross-react with rabbit and human LIF such as the mouse monoclonal antibody clone 9824.11 raised against human LIF. Preferably, the concentration of LIF is less than 1 ng/ml, more preferably less than 0.5 ng/ml, still more preferably less than 0.2 ng/ml, still more preferably less than 0.1 ng/ml, still more preferably less than 0.05 ng/ml and most preferably the concentration of LIF is less than 0.02 ng/ml LIF as determined with said assay. The composition can include a basic cell culture medium such as, but not limited to, a medium comprising high glucose DMEM with further optional addition of one or more of the compounds selected from non-essential amino acids, glutamine, a reducing agent and fetal, newborn or adult serum such as fetal bovine serum. The cells used for conditioning the medium are cells such as immortal fibroblast cell line such as the rabbit fibroblast cell line Rab9 (ATTC CRL-1414).

In another aspect of the invention, the composition for deriving, maintaining and growing pluripotent and germline competent human or non-human mammalian embryonic stem cells is a composition comprising a conditioned medium from certain cells transfected with a nucleotide sequence encoding LIF. Said nucleotide sequence encodes for mammalian LIF and preferably encodes for rabbit LIF. Said nucleotide sequence can be a cDNA sequence but is preferably a genomic sequence of the mammalian LIF. The transfected cell line is preferably stably transfected with the LIF encoding nucleotide sequence. The cells used for transfecting a nucleotide sequence encoding for LIF can be any mammalian cell but is preferably a fibroblast cell, more preferably a rabbit fibroblast cell line and most preferably the rabbit Rab9 (ATCC CRL 1414). The transfected cells used in this invention are rabbit Rab9 fibroblast cells which are stably transfected with a genomic sequence encoding for rabbit LIF. Such a cell line has been deposited with the Belgian Coordinated Collection of Microorganisms, Belgium under accession number LMBP 5479CB. The composition can include a basic cell culture medium such as, but not limited to, a medium comprising high glucose DMEM with further optional addition of one or more of the compounds selected from non-essential amino acids, glutamine, a reducing agent and newborn or adult serum and a fetal serum other than bovine fetal serum such fetal horse serum, fetal goat serum, fetal sheep serum.

In a third aspect of the invention, the composition for deriving, maintaining and growing pluripotent and germ-line competent human or non-human mammalian embryonic stem cells is a composition comprising a conditioned medium from certain cells and wherein the composition is supplemented with rabbit LIF, a protein with at least 95% similarity to rabbit LIF or a functional derivative thereof. Said protein may be expressed in a yeast suitable for protein expression such as the methylotrophic yeast *Pichia pastoris* and wherein the nucleotide sequence encoding for said protein is optionally adapted in order to obtain an optimized sequence for use in the yeast expression system. The rabbit LIF disclosed in this invention is produced by the *Pichia pastoris* strain, which has been deposited at the Belgian Coordinated Collection of Microorganism, Belgium under accession number MUCL-49925.

The composition can include a basic cell culture medium such as, but not limited to, a medium comprising high glucose DMEM with further optional addition of one of the compounds selected from non-essential amino acids, glutamine, a reducing agent and fetal, newborn or adult serum such as fetal bovine serum.

The present invention discloses the use of these compositions for the generation of multipotent or pluripotent embryonic stem cells of non human mammals such as but not limited to mouse and more specifically to *Mus musculus* strains selected from the group 129/SvEv, C57BL/6N, C57BL/6J-HPRT, BALB/cAnN, CBA/CaOIa, 129/SvJ, DBA/2N, DBA/1OIa, C3H/HeN, C57BL/6JOIa, FVB/DBA1LacJ, CD1, BALB/c, MRL, C57BL/6×CBA and Swiss Webster genetic background.

The present invention relates further to multipotent or pluripotent embryonic stem cells of human or non human mammals such as but not limited to mouse and more specifically to *mus musculus* strains selected from the group of 129/SvEv, C57BL/6N, C57BL/6J-HPRT, BALB/cAnN, CBA/CaOIa, 129/SvJ, DBA/2N, DBA/1OIa, C3H/HeN, C57BL/6JOIa, FVB/N, DBA1LacJ, CD1, BALB/c, MRL, C57BL/6×CBA, and Swiss Webster genetic background which are obtained by culturing them for at least one passage in the compositions of the present invention.

The present invention relates further to transgenic non human mammals such as but not limited to mouse and more specifically to *mus musculus* strains selected from the group of 129/SvEv, C57BL/6N, C57BL/6J-HPRT, BALB/cAnN, CBA/CaOIa, 129/SvJ, DBA/2N, DBA/1OIa, C3H/HeN, C57BL/6JOIa, FVB/N, DBA1LacJ, CD1, BALB/c, MRL, C57BL/6×CBA and Swiss Webster genetic background which are obtained by culturing the embryonic stem cells used for the generation of said animals for at least one passage in the compositions of the present invention.

The present invention relates further to methods for producing the compositions, embryonic stem cells and transgenic animals disclosed in this invention.

The present invention discloses the use of media conditioned by rabbit cell lines for the generation of embryonic cells and transgenic animals and is applicable to other non human mammals such as non-human primates, pigs, sheep, cows, mink, horses, goats, sheep, cats, dogs rabbits, rats, hamsters and rodents other than the mouse *Mus musculus*.

The present invention further discloses methods to obtain embryonic stem cell lines for 30 or more percent of explanted blastocysts.

The present invention also discloses methods to obtain adult progeny via aggregation cells with embryonic stem cells that have been cultivated for at least 16 passages.

The present invention is particularly directed to novel compositions for deriving, maintaining and growing pluripotent and germ-line competent mammalian embryonic stem cells. The compositions include a basic cell culture medium such as, but not limited to, a medium comprising high glucose DMEM, non-essential amino acids, glutamine, a reducing agent and fetal bovine serum, or equivalents thereof, which are preconditioned by a stable cell line such as, but not limited to, the rabbit cell line Rab9 (ATCC CRL-1414) or equivalents thereof, which secrete essential elements for growth and self renewal of ES cells. It has been found that this conditioned media with low amounts and even in the absence of LIF supports self-renewal of ES cells and allows ES cell derivation. Maintenance of the undifferentiated state, as evidenced by morphological and surface marker criteria (presence of alkaline phosphatase and absence of vimentin and cytokeratin), was superior to that observed with standard cell culture media to which murine LIF or rabbit LIF was added.

To this composition purified recombinant Leukemia Inhibitory Factor (LIF) can optionally be added, preferably rabbit LIF (Rab-LIF) disclosed in the present invention, or alternatively commercially available LIF. Antibiotics, such as penicillin/streptomycin, and insulin, may also be included in the composition. The present invention is also directed to a novel rabbit LIF (Rab-LIF) that maintains ES cells undifferentiated in vitro culture and to nucleotides encoding the Rab-LIF. Other ingredients may optionally be included in the ES medium, such as interleukins, oncostatins, neurotrophic factors, stem cell factors and fibroblast growth factors. Specific examples of these factors are human Interleukin 11, human oncostatin M, human ciliary neurotrophic factor, cardiotrophin, Interleukin 6 with its specific receptor and human stem cell factor. The invention further relates to the use of these ES cell lines for germline transmission and for the generation of genetically modified non-human animals.

The invention further relates to the use of the novel compositions of the present invention for the isolation, maintenance and expansion of primordial germ cells.

The invention also relates to compositions for the stroma free expansion of mammalian adult stem cells or early progenitor cells. Examples hereof are hematopoietic stem cells and the adult early hematopoietic progenitor cells The compositions for cultivating ASC comprise conditioned medium of a fibroblast cell line. The fibroblast cell lines is preferably an immortalised cell line, more preferably a rabbit. immortalised fibroblast cell and most preferably the Rab9 (ATCC CRL1414) cell line. The compositions for cultivating ASC preferably comprises no added cytokines and/or LIF.

The invention also relates to the use of the compositions for expanding ASC or early progenitors cells, such as HSC. These HSC are for example CD34+ cells which have been isolated from as source such as umbilical cord, placental blood, peripheral blood and bone marrow. With the use of the compositions the total amount of cells are expanded by at least 25 fold. With the use of the compositions the amount of CD34+ cells is expanded by at least 3 fold. With the use of the compositions the expanded cells are cultivated for at least 15 days. With the use of the compositions the number of expanded cells which respond positively in an LTC IC assay is increased by at least 15.

The invention further relates to a method for expanding mammalian adult stem cells or early progenitor cells comprising the steps of isolating a source of mammalian adult stem cells or early progenitor cells and cultivating the cells under stroma free conditions in a composition according to the present invention for cultivation ASC. This method can be applied to hematopoietic stem hematopoietic precursor cells. This method can be performed until an expansion of the ASC by at least 25 fold is obtained. This method can be performed until the amount of nucleated cells is expanded by at least 10 fold. This method can be performed until the amount of CD34+ cells have been expanded by at least 3 fold This method can be performed for at least 15 days This method can be performed until the number of expanded cells which respond positively in an LTC IC assay is increased by at least 15 fold. This method can be performed in order to obtain expanded HSC cells which can repopulate a sublethal irradiated NOD/SCID (Non Obese Diabetic/Severe Combined Immunodeficient) mouse.

The present invention also relates to the use of media conditioned by a stable cell line for the expansion of hematopoietic stem cells from bone marrow, fetal blood umbilical cord blood and peripheral blood. The compositions include a basic cell culture medium such as, but not limited to, a medium comprising high glucose DMEM, non-essential amino acids, glutamine, a reducing agent and fetal bovine serum, or equivalents thereof, which are preconditioned by a stable cell line such as, but not limited to, the rabbit cell line Rab9 (ATCC CRL-1414) or equivalents thereof, which secrete essential elements for growth and self renewal of hematopoietic stem cells.

The present invention will now be described with reference to the following drawings.

BRIEF DESCRIPTION OF THE DRAWINGS

FIG. 1 shows the nucleotide sequence [SEQ. ID.: NO 1] of rabbit LIF (Rab-LIF) cDNA along with the peptide sequence thereof [SEQ. ID.: NO 2].

FIG. 2 shows the nucleotide [SEQ. ID.: NO 3] and amino acid [SEQ. ID.: NO 4] sequence of rabbit LIF cDNA optimized for expression in *Pichia pastoris*.

DEFINITIONS

Figure 3:
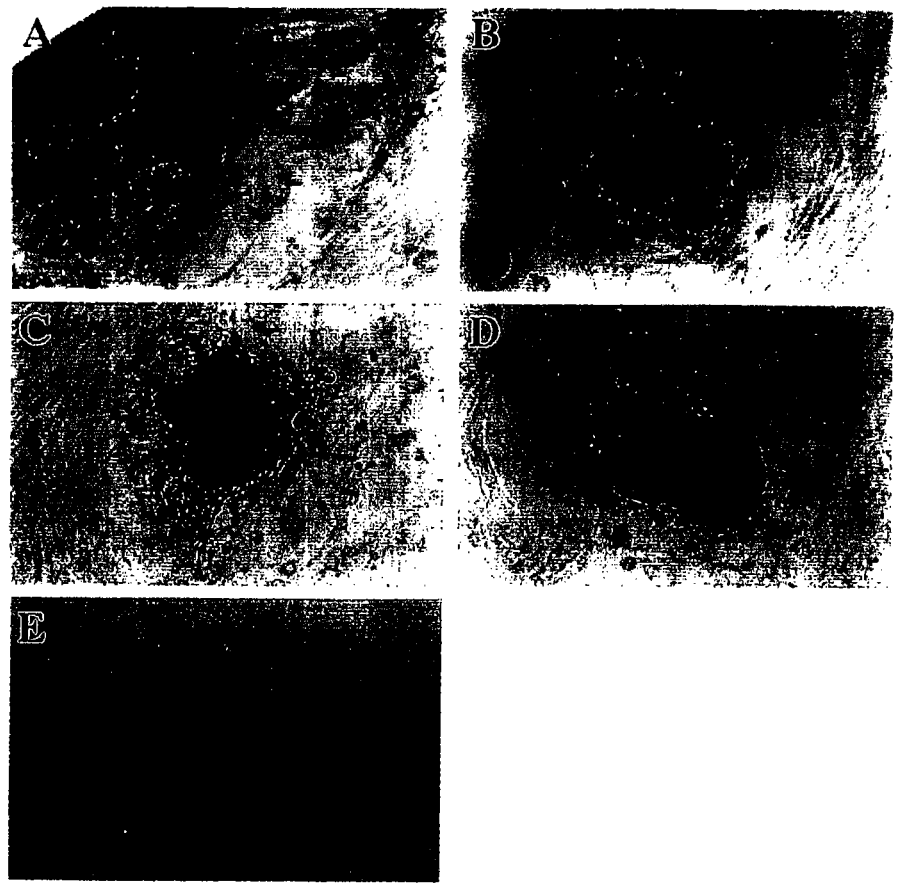
FIG. 3 shows the initial outgrowth (passage 0) of attached blastocysts from C57BL6/N mouse, when cultured in A) enriched basic medium with added murine LIF (1,000 IU/ml); B) enriched basic medium with added Rab-LIF (10-20 ng/ml); C) basic medium conditioned on Rab9 fibroblast cells; D) basic medium conditioned on the Rab9 #19 fibroblast cell line; E) enriched basic medium.

Embryonic stem (abbreviated ES) cells in the present invention are cell lines isolated from the inner cell mass (ICM) of blastocyst-stage embryos or derived from the primordial germ cells from a post-implantation embryo (primordial or embryonal germ cells). ES cells can be maintained under specific conditions in culture for many passages without loss of their pluripotency.

Pluripotent or multipotent in the present invention means that stem cells can give rise to different types of cells and tissue including cells and tissues supporting the pregnancy but are unable to give rise to cells of the germ line (sperm cells and egg cells).

Germ line competent, totipotent or omnipotent in the present invention means that stem cells can give rise to all types of cells and tissue including cells of the germ line (sperm cells and egg cells)

Leukemia Inhibitory Factor (LIF) as used herein refers to a mammalian protein, originally cloned and sequenced by Gearing et al. (1987) EMBO J. 6, 3995-4002 which enables the derivation, growth and maintenance of undifferentiated embryonic stem cells derived from the inner cell mass of blastocysts. It refers also to splice variants of LIF and to variants of LIF wherein one or more amino acids are mutated, inserted or deleted with the restriction that the variant LIF is at least 95% identical to wild type LIF and that it enables the derivation, growth and maintenance of undifferentiated embryonic stem cells derived from the inner cell mass of blastocysts.

Functional protein fragment of LIF as used herein refers to a LIF protein with N or C terminal deletions, which still enable the derivation, growth and maintenance of undifferentiated embryonic stem cells derived from the inner cell mass of blastocysts.

"not enriched with cytokines and/or LIF" in the present invention in the context of ASC means that the composition wherein cells are maintained or expanded, is not enriched with additional cytokines or LIF. Addition or enrichment means supplementation to the composition of cytokines or LIF as a protein. It also means the supplementation of these compounds via the transient or stable transfection of cells which are used for the conditioning of the medium.

"adult stem cells" as used herein relates to multipotent adult stem cells isolated from a mammal, such as rodents (e.g. mouse and rat) and primates, especially humans. Adult stem cells or derived from a non-embryonic organ or tissue and have the capacity to be induced to differentiate to form at least one differentiated cell type of mesodermal, ectodermal and endodermal origin. The organ or tissue from which the adult stem cells are isolated are for example, but not limited to, bone marrow, umbilical cord blood or placenta. The different types of cells that can be obtained from adult stem cells are depending, from the type of adult stem cell, for example osteoblasts, chondrocytes, adipocytes, fibroblasts, marrow stroma, skeletal muscle, smooth muscle, cardiac muscle, ocular, endothelial, epithelial, hepatic, pancreatic, hematopoietic, glial, neuronal or oligodendrocytes.

"adult early progenitor cells" in the present invention refers to committed cells which have lost one or a few of the markers of the stem cell they originate from, but are still able to differentiate in a number of cell lineages, but less than the stem cell they are derived from.

"hematopoietic stem cell" (abbreviated as HSC) is a cell isolated from peripheral blood, umbilical cord blood or bone marrow that can renew itself, can differentiate to a variety of specialized cells. HSCs can repopulate the erythroid, neutrophil-macrophage, megakaryocyte and lymphoid hemopoietic cell pool. HSC express CD34, c-kit and thy1, but do not express CD38.

Deposits of Cell Lines

The *P. pastoris* X33 (RbL) expressing rabbit LIF was deposited with accession number MUCL42925) on Jul. 5, 2000, by Thromb-X (Leopoldstraat 1, 3000 Leuven, Belgium) in the Belgian Coordinated Collections of Microorganisms (BCCM) Mycothèque de l'Université Catholique de Louvain (MUCL) PlaceCroix du Sud, B 1348 Louvain la Neuve, Belgium.

The rabbit fibroblast cell line expressing rabbit LIF (Rab9#19 clone) was deposited with accession number LMBP 5479CB) on Apr. 7, 2000 by Thromb-X (Leopoldstraat 1, 3000 Leuven, Belgium) in the Belgian Coordinated Collections of Microorganisms (BCCM) Laboratorium voor Moleculaire Biologie-Plasmidencollectie (LMBP) Universiteit Gent, K.L.Ledeganckstraat 35, 9000 Gent, Belgium.

DETAILED DESCRIPTION OF THE INVENTION

The present invention relates to the use of the disclosed compositions for the derivation, maintenance and growth of pluripotent and germline-competent mammalian embryonic stem (ES) cell lines, as exemplified in mouse strains. These improved culture conditions can be used to generate stable murine ES cells from many different genetic backgrounds, with superior potential for germline transmission. This technology is also applicable to other non human mammalian species (rabbits, pigs, cattle, etc.) and can form the basis for targeted transgenesis with gain-of-function or loss-of-function in non-murine species.

The compositions consist of a basic cell culture medium, which is preconditioned by a stable cell line, that secretes essential elements for growth and self-renewal of ES cells. To these compositions purified recombinant Leukemia Inhibitory Factor (LIF) can optionally be added, e.g. in low amounts.

In one embodiment, the basic cell culture medium is high glucose Dulbecco's modified Eagle's medium DMEM, with non-essential amino acids, glutamine, beta-mercaptoethanol and fetal bovine serum, and the stable cell line is a rabbit fibroblast-like cell line Rab9 (ATCC CRL-1414). The optional addition of LIF preferably consists of the newly disclosed rabbit LIF (Rab-LIF) which helps maintain ES cells undifferentiated in in vitro culture, and which is obtained by expression of an optimized cDNA sequence in *Pichia pastoris*.

LIF secreted by cells into the medium can be determined via a quantitative immunoassay such as linked immuno sorbent assay (ELISA), a radio immunoassay (RIA), an immuno radio metric assay (IRMA), a fluorescent immunoassay (FIA), a chemiluminescent immuno assay (CLIA) or an electro chemiluminescent immuno assay (ECL) using antibodies against LIF. In this invention an ELISA using a monoclonal antibody with reactivity against rabbit LIF, such as the mouse monoclonal antibody Clone 9824.11 raised against human LIF, is preferred as a reference. An example of such an assay is the Quantikine Human LIF immunoassay (Cat No DLF00, R&D Systems Minneapolis, Minn., USA).

The compositions of the invention may have a varying amount of additional constituents provided that their amount is sufficient to maintain ES cells undifferentiated for prolonged periods in culture The composition of the invention comprises conditioned medium of the fibroblast-like cell line in a medium selected but not limited to Phosphate Buffered Saline (PBS), Dulbecco's Modified Eagle Medium (DMEM), Iscove's Modified, Dulbecco's medium, McCoy 5A medium, Minimal Essential Media Eagle (MEM), RPMI 1640, Medium 199, MCDB Medium, RPMI, Glasgow minimum Essential Media Eagle (GMEM), DMEM/F-12 Media, Hams F-10 Nutrient mixture, Leibovitz's L15 Media, CMRL Media, BGJb Medium, Basal Medium Eagle (BME), Brimster's BMOC-3 Medium, William's Media E and McCoy's Media or adaptations thereof. To the composition further a reducing agent such as beta-mercapto ethanol or dithiothreitol.

In the composition containing conditioned medium of cells, which are not transfected with DNA encoding LIF, the medium is supplemented with adult, newborn or fetal serum. In the composition with conditioned medium from cells transfected with DNA encoding LIF, the serum can be adult or newborn mammalian serum or non bovine fetal serum such as horse, goat and sheep fetal serum.

A preferred example of a composition of the invention comprises per liter conditioned medium of the fibroblast-like cell line, an added volume of 50 to 120, preferably 80 ml of fetal bovine serum, 10 to 25, preferably 17 ml non-essential amino acids, 2 to 8, preferably 5 μl β-mercaptoethanol, 0.5 to 2.5, preferably 1.25 ml insulin, and 80 to 130 ml basal ES cell medium.

Preferably, the basal ES cell medium consists of 400 to 600, preferably 500 ml DMEM high glucose, 0 to 15, preferably 13 ml penicillin/streptomycin, 10 to 15, preferably 13 ml non essential amino acids, 10 to 15, preferably 13 ml glutamine, 5 to 10, preferably 6.3 μl β-mercaptoethanol, 50 to 100, preferably 70 ml fetal bovine serum, neutral pH of preferably 7.4.

The invention further relates to processes to derive and to culture mammalian ES stem cells to obtain pluripotent and germline-competent ES cells, wherein the culturing of the mammalian ES stem cells is at least partially performed in a composition according to the invention and described above. Such a process comprises the steps of: a) culturing cells of blastocyst stage embryos; b) culturing isolated inner mass cells; and c) passaging the inner mass cells periodically in a composition of the invention. Preferably, the inner mass cells are periodically passaged for at least 8 times. The process may further comprise the step of producing transgenic animals.

According to a further aspect thereof the invention relates to embryonic stem (ES) cell lines with germline transmission capability. The cell line is preferably a murine cell line, but other animal cell lines are also possible. In case of a murine cell line, the cell line can be derived from cells or tissues of 129/SvEV, C57BL/6N, C57BL/6J-HPRT, BALB/cAnN, CBA/CaOla, 129/SvJ, DBA/2N, DBA/1CaOla, C3H/HeN, C57BI/6Ola, FVB/N, DBA1LacJ, CD1, BALB/c, MRL, C57BL/6×CBA, or Swiss Webster genetic backgrounds. The murine cell lines preferably have a germline transmission capability after 11 or more passages. The embryonic stem (ES) cell lines of the invention are characterized by three dimensional colony formation, positive staining for alkaline phosphatase and negative staining for cytokeratin 18 and vimentin after more than 10 passages. These embryonic stem (ES) cell lines may be used in the generation of chimeric or ES cell derived animals, in the gene alteration by homologous or non-homologous recombination, in the generation of animals with gene alteration via germline transmission, for the generation of chimeric animals, for the generation of chimeric animals following blastocyst injection into recipient blastocysts or diploid or tetraploid embryo aggregation, or nuclear transfer, for the study or isolation of (novel) genes or for the expression or overexpression of genes.

The compositions of the present invention show superior characteristics in maintaining the phenotype of embryonic stem cells of different mice strains. The present invention also shows that the properties of these novel compositions also apply to stem cells other than embryonic stem cell.

The present invention thus, relates to the use of the disclosed compositions for the maintenance and growth of adult stem cells and early progenitor cells, as exemplified with HUC derived CD34+ cells.

In one embodiment of the invention cultures of adult stem cells or adult early progenitors cells are maintained and expanded in the compositions of the present invention under stroma free conditions, this is in the absence of a direct contact with feeder cells or in the absence of an indirect contact with feeder cells (non contact cultures). The compositions for the expansion of ASC according to the present invention are conditioned by fibroblast cells, preferably immortalized fibroblast cells, and more preferably rabbit immortalized fibroblast cells such as the Rab9 cell line (ATCC CRL-1414). The present invention shows that these compositions are superior over basal ES media for the proliferation and maintenance of adult stem cells or early progenitor cells such as HSC or hematopoietic precursor cells. The compositions can comprise additional LIF (added protein, or LIF produced by transfected cells used for conditioning the medium). In a preferred embodiment however, the compositions for adults stem cells have no added LIF. On one hand, the absence of LIF has does have an influence on the proliferation capacity of ASC capacity. On the other hand the presence of LIF is known to stimulate the differentiation of cells such HSC into the myeloid lineage. The absence of LIF has a thus a positive effect on maintaining the undifferentiated properties of at least HSC or early hematopoietic progenitor cells.

In a more preferred embodiment of the invention the compositions for the cultivation of ASC have not been enriched, that is have no added cytokines or growth factors. Cytokines or growth factors which are typically added to media for cultivating for example HSC or hematopoietic precursor cells are for example Flt3 ligand, IL-6 (Interleukin), soluble IL-6 receptor, Tpo (thrombopoetin), SCF (stem cell factor), Interleukin-7, Interleulin 8, G-CSF (granulocyte colony-stimulating factor)(MIP-1a) macrophage-inflammatory protein-1a, MCP (monocyte-chemoattractant protein-1) (VEGF) vascular endothelial cell growth factor. In accordance with the present invention the addition of cytokines such as mentioned above, can be omitted for the proliferation and maintenance of adult stem cells or early progenitor cells such as HSC or hematopoietic precursor cells.

Thus, in a preferred embodiment of the invention the composition for cultivating ASC such as HSC is performed in a composition to which neither LIF, neither cytokines are added.

In one embodiment of the invention the compositions of the present invention are used for maintaining the phenotype of adult stem cells and adult early progenitors cells. As an example hereof the invention describes the applicability of maintaining for a prolonged period the stem cell properties of HUC (human umbilical cord) derived hematopoietic stem cells.

Adult stem cells and/or early progenitor cells such as HSC or early hematopoietic precursor cells can, according to the present invention be passaged after isolation for at least 15 days in culture, preferably at least 30 days in culture, more preferably for at least 60 days in culture, even more preferably for at least 90 days in culture and even more preferably for at least 180 days in culture.

Adult stem cells and/or early progenitor cells such as HSC or early hematopoietic precursor cells can, according to the present invention be expanded by at least 10 fold, preferably by at least 25 fold, more preferably by at least 40 fold, even more preferably by at least 100 fold, and most preferably by at least 1000 fold.

The amount of CD34+ adult stem cells and/or early progenitor cells such as HSC or early hematopoietic precursor cells can, according to the present invention be expanded by at least 5 fold, preferably by at least 10 fold, more preferably by at least 50 fold, even more preferably by at least 250 fold, and most preferably by at least 1000 fold.

The potential of expanded adult stem cells and/or early progenitor cells such as HSC or early hematopoietic precursor cells can, according to the present invention be expanded by at least 5 fold, preferably by at least 15 fold, more preferably by at least 50 fold, even more preferably by at least 250 fold, and most preferably by at least 1000 fold as assayed by an assay such as the LTC IC assay wherein the capacity to expand into myeloid progenitors is evaluated.

The expanded ASC such as HSC can after cultivation for at least 15 days, preferably at least 28 days, and more preferably for at least 60 days and most preferably for at least 90 days, engraft sublethal irradiated NOD/SCID mice The HSC cells which are cultivated according to the present invention are can be serially passaged to secondary NOD/SCID mice.

The invention will be illustrated in the following examples that are not intended to limit the scope of the invention. Based on the present invention, several variations and improvements will be obvious to those skilled in the art.

EXAMPLES

Example 1

Production of Recombinant Rabbit Leukemia Inhibitory Factor (Rab-LIF)

The above-referenced method and ES cell medium can optionally include LIF, preferably recombinant Rab-LIF, to help maintain ES cells undifferentiated and capacity to produce germline transmission. In FIG. 1, the nucleotide sequence of Rab-LIF is provided along with the peptide sequence thereof.

Rab-LIF may be prepared by a number of methods, typically by one of the many molecular biological tools, i.e., expression systems, available to biologists. In such a case, DNA molecules encoding Rab-LIF protein may be operably linked to DNA molecules encoding a transcription promoter and terminator to create an expression cassette. The DNA molecule containing the promoter, terminator and Rab-LIF-encoding DNA may then be introduced into a cell for production of the Rab-LIF protein. Preferably, a DNA encoding a secretion signal is operably linked to the Rab-LIF-encoding DNA in such a manner that active Rab-LIF is secreted from the cell.

The promoter may be constitutive, inducible or tissue-specific, the choice of which typically depends upon the cells in which it is desired to produce the Rab-LIF protein, and under which conditions. As described herein in Example 1, recombinant Rab-LIF is produced in *Pichia pastoris* and is operably linked with the yeast alpha factor secretion signal, and the alcohol oxidase 1 (AOX1) promoter. Alternatively, the Rab-LIF-encoding DNA may be operably linked to appropriate promoters, enhancers or terminators (collectively, "control sequences") for expression in prokaryotic cells or higher eukaryotic cells such as mammalian cells and insect cells.

Recombinant Rab-LIF was produced using the methylotrophic yeast *Pichia pastoris* expression system from Invitrogen (Carlsbad, Calif.). The Rab-LIF gene was isolated from a rabbit genomic library Lambda DASH II (Stratagene, #945950) and the cDNA encoding the mature Rab-LIF protein was assembled by spliced overlap extension polymerase chain reaction (SOE-PCR) using standard procedures.

The Rab-LIF cDNA was used as template in consecutive PCR and SOE-PCR reactions to optimize the gene for expression in *P. pastoris*, by modifying the codon usage. The nucleotide sequence of this Rab-LIF optimized cDNA is shown in FIG. 2.

The primer in the PCR reaction was designed to allow precise in frame fusion of the mature Rab-LIF sequence with the alpha factor secretion signal in the pPICZα vector (Invitrogen). This allows the isolation of the recombinant protein from transformed *Pichia pastoris* culture supernatant. This primer introduced also an extra alanine codon (underlined in the sequence above) in front of the mature Rab-LIF coding sequence to facilitate the Kex2 processing of the alpha factor secretion signal. The LY-RLIF-PD primer contained a NotI site. The product was purified, digested with XhoI and NotI, and cloned in the corresponding sites of the vector pPICZα, yielding pPICZα-RLIF100. In this vector, expression of the Rab-LIF is directed by the strong alcohol oxidase I (AOX1) promoter.

Prior to transformation in *P. pastoris*, the vector pPICZα-RLIF100 was linearized by digestion with BstX1, cutting in the 5' AOX1 untranslated sequence, to allow stable integration of the expression module in the AOX1 chromosomal locus. All the yeast manipulation was further performed as recommended by the supplier. The *P. pastoris* transformant X33 (RbL) was finally selected as Rab-LIF yeast expression strain and deposited in the Belgian Coordinated Collections of Microorganisms with accession number MUCL42925)

It should be noted that the expression cassette described above is stably integrated in the chromosome. The X33 (RbL) strain was deposited in the BCCM Collection on Jul. 5, 2000. The optimized nucleotide sequence for expression in *Pichia* forms a part of the present invention.

The nucleotide sequence and amino acid sequence of the Rab-LIF cDNA, which has not previously been reported, are shown in FIG. 1. The nucleotide sequence was determined according to the standard method of Sanger et al.

The Rab-LIF nucleic acid sequence of the mature protein was manually compared to the human LIF sequence (Gough et al. 1988, accession M63420 & J05436 and mouse LIF sequence (Gearing et al. 1987, accession M63419 & J05435.) A homology of 90% was found between the nucleic acid sequence of human and rabbit LIF. A homology of 77% was found between the nucleic acid sequence of mouse and rabbit LIF. The corresponding homologies of the optimized cDNA for expression in *Pichia pastoris* were 61% with murine and 70% with human LIF.

Example 2

Production of ES Cell Culture Medium Preconditioned with Rab9

In one embodiment of the present invention, basic ES cell medium, conditioned by confluent monolayer cultures of the Rab9 fibroblast cells, is collected for 4 consecutive days and the conditioned media are pooled for use in ES cell culture. Each day 15 cm Petri dishes are refreshed with 25 ml of basic ES medium. After 4 days each 15 cm Petri dish is split at a ratio of 1 to 4. The first day after splitting, the medium is discarded. To 1 liter of conditioned basic ES medium (from the mixture of the 4 collection days), 80 ml fetal bovine serum, 17 ml non-essential amino acids, 20 ml glutamine, 6.3 µl-mercaptoethanol, 1.25 ml insulin and 80 ml basal medium is added and the pH is adjusted to 7.4. The basic medium was composed of: 500 ml DMEM high glucose, 70 ml fetal bovine serum, 13 ml penicillin/streptomycin, 13 ml glutamine, 6.3 µl β-mercaptoethanol, and 13 ml non-essential amino acids. Enriched basic medium is basic medium to which another 4% (v:v) fetal bovine serum is added.

In other embodiments, the production of conditioned basic ES medium can be scaled up using standard procedures such as roller bottles, cell factories or bioreactors.

Example 3

Derivation and Culture of Murine Embryonic Stem (ES) Cells

1. Mouse Strains and ES Cells

ES cells can be derived amongst others from the following commercially available mouse strains: 129/SvEvTaconic (Taconic, Germantown, N.Y., USA); C57BL/6NTacfBr (Taconic); BALB/cAnNTacfBr (Taconic); DBA/2NTacfBR (Taconic); C3H/HeNTac MTVfBe (Taconic); FVB/NTacfBR (Taconic); Tac:(SW)fBR, Swiss Webster (Taconic); 129/SvJ (The Jackson Laboratory, Bar Harbor, Me., USA); C57BL/6J-HPRT <B-M3> (The Jackson Laboratory); C57BL/6JOI-aHsd (Harlan, Indianapolis, Ind., USA); CBA/CaOIaHsd (Harlan); DBA/1OIaHsd (Harlan), DBA1LacJ, CD1, BALB/c, MRL, C57BL/6×CBA.

2. Derivation of Murine ES Cells

ES cells can be derived from 3.5-4.5 days old blastocyst stage murine embryos, which can be collected and plated individually on a 96 well dish covered with a mitotically arrested mouse embryonic fibroblast feeder monolayer. The blastocysts are allowed to attach to the monolayer, and refed every day with conditioned ES cell medium of the present invention (see Example 2), with basic ES medium with or without addition of murine LIF or Rab-LIF, or with ES cell medium conditioned with the Rab9#19 cell line which secreted endogenous Rab-LIF (see below).

After 5-6 days in culture, the inner cell mass (ICM) outgrowth is selectively removed from the (remaining) trophectoderm and replated after trypsinization with trypsin-EDTA on a 96 well dish with mitomycin arrested murine fibroblasts. Subsequently the ES cells are gradually plated on larger culture dishes. ES cells can remain undifferentiated for more than 20 passages by using conditioned ES cell medium of the present invention.

Fibroblast feeder layers can be obtained from murine embryos of 12.5 days post-coitus pregnant mice. The mice are sacrificed, and the uteri collected and placed in a petri dish containing phosphate buffered saline (PBS). The embryos are dissected out of the uterus and all membranes removed. The embryos are transferred into a new dish containing PBS, the head and all internal organs removed and the carcasses washed in PBS to remove blood. The carcasses are then minced using 2 insulin syringes into cubes of 2 to 3 mm in diameter, and incubated in Trypsin-EDTA/MEM solution (10/90 VN) at 4° C. for 2 hrs. The suspension is then incubated at 37° C. for 15 min, a single cell suspension made using a 5 ml pipette, and plated at $5 \times 10^6$ cells per 1.80 mm petri dish in 25 ml Feeder Medium.

Feeder Medium consisted of 500 ml Dulbecco's Minimal Essential Medium (DMEM), 10% fetal calf serum (FCS), 13 ml penicillin/streptomycin, 13 ml glutamine, 13 ml non-essential amino acids, 2.3 µl β-mercaptoethanol. The medium is changed after 24 hr to remove debris. After 2 to 3 days of culture the fibroblasts reaches a confluent monolayer. The plates are then trypsinized, replated on 2 petri dishes, and, when confluent, the cells of each plate are frozen in 2 vials, kept at −80° C. overnight and transferred to liquid nitrogen the next day.

3. Culture of ES Cells

ES cells are grown to subconfluency on mouse embryonic fibroblasts mitotically arrested with mitomycin. Culture dishes are kept at 39° C. in a humidified atmosphere of 5% $CO_2$ in air. The ES cells are passaged every 2-3 days onto freshly prepared feeder dishes. The ES cells are fed every day with the conditioned ES cell medium.

4. Comparison

In one aspect of the invention, the blastocysts were obtained from the natural matings of C57BL/6N TacfBr (Taconic) mice. The blastocysts were cultured with: a) enriched basic medium (see below); b) enriched basic medium with added murine LIF (10001 U/ml); c) enriched basic medium with added Rab-LIF (10 ng/ml); d) enriched basic medium with added Rab-LIF (20 ng/ml); e) basic medium conditioned on Rab9 fibroblast cells according to example 2; or f) basic medium conditioned on the Rab9 #19 fibroblast cell line (see below).

The basic medium was composed of: 500 ml DMEM high glucose, 70 ml fetal bovine serum, 13 ml penicillin/streptomycin, 13 ml glutamine, 6.3 μl β-mercaptoethanol, and 13 ml non-essential amino acids. Enriched basic medium is basic medium to which another 4% (v:v) fetal bovine serum is added.

The basic medium conditioned by the Rab9 fibroblast cells is obtained as illustrated in Example 2. To 1 liter of conditioned basic ES medium (from the mixture of the 4 collection days), 80 ml fetal bovine serum, 17 ml non-essential amino acids, 20 ml glutamine, 6.3 μl β-mercaptoethanol, 1.25 ml insulin and 80 ml basal medium is added and the pH is adjusted to 7.4. This conditioned medium contains unmeasurable level (less than 20 pg/ml) of Rab-LIF as determined with the ELISA for human LIF of R&D Systems (Minneapolis, Minn., USA).

Basic medium, conditioned by the Rab9#19 fibroblast cells, is collected for 4 consecutive days as described for Rab9 in Example 2. To 1 liter of conditioned basic ES medium (from the mixture of the 4 collection days), 80 ml fetal bovine serum, 17 ml non-essential amino acids, 20 ml glutamine, 6.3 μl β-mercaptoethanol, 1.25 ml insulin and 80 ml basal medium is added and the pH is adjusted to 7.4. Rab9#19 are Rab9 fibroblast cells which have been stably transfected with the rabbit Leukemia Inhibitory Factor gene and which secrete up to 30 ng/ml/day of Rab-LIF in the medium as determined with the ELISA for human LIF of R&D Systems (Minneapolis, Minn., USA).

The blastocysts are allowed to attach to the feeder layer. The culture medium is refreshed every day. After approximately 1 week in culture, the ICM outgrowth is removed from the trophectoderm and after trypsinization passed onto a new 96 well dish covered with a feeder layer of mitomycin C arrested murine fibroblasts. The ES cells are subsequently gradually passed onto larger culture dishes with a feeder layer. After 5 to 10 passages, the number of established ES cell lines is counted for each of the culture conditions. The undifferentiated character of the established ES cell lines is determined by immunochemical staining for the presence of alkaline phosphatase (Vector Laboratories Inc., Burlingame, Calif.), or for the absence of vimentin and cytokeratin (both Dako A/S, Denmark). Only ES cell lines, which consist for more then 90% of undifferentiated cells are maintained in culture.

Figure 4:
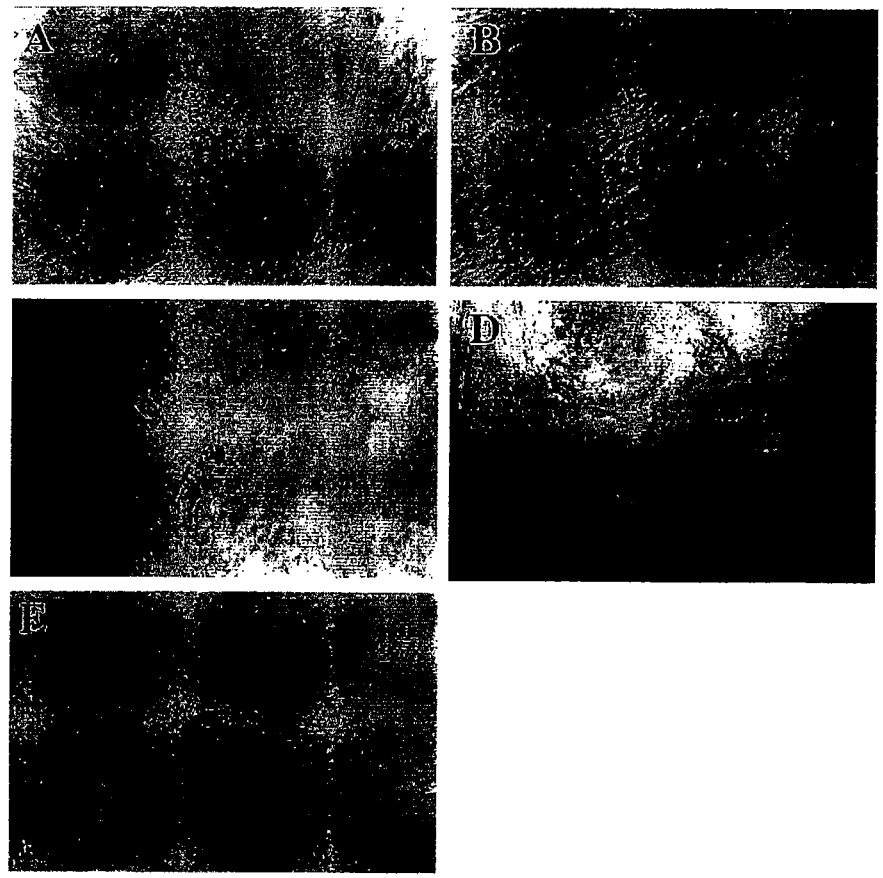
FIG. 4 shows the morphology of ES cell colonies after 1 passage in A) enriched basic medium with added murine LIF (1,000 IU/ml); B) enriched basic medium with added Rab-LIF C) basic medium conditioned on Rab9 fibroblast cells; D) basic medium conditioned on the Rab9 #19 fibroblast cell line; E) enriched basic medium.

Enriched basic medium alone did not allow ES cell derivation. ICM outgrowth rapidly differentiated before or during the first passage (FIG. 3E and FIG. 4E).

TABLE I

Efficiency of murine C57BL6/N ES cell derivation

| Culture medium | Number of blastocysts explanted | Number of ES cell lines established | |
|---|---|---|---|
| | | Number | % |
| Enriched basic medium | 21 | 0 | 0% |
| Enriched basic medium with added murine LIF (1000 IU/ml) | 26 | 6 | 23% |
| Enriched basic medium with added Rab-LIF (10 ng/ml) | 21 | 6 | 28% |
| Enriched basic medium with added Rab-LIF (20 ng/ml) | 22 | 5 | 23% |
| Basic medium conditioned on Rab9 fibroblast cells | 35 | 17 | 48% |
| Basic medium conditioned on the Rab9 #19 fibroblast cell line | 18 | 9 | 50% |

When either murine LIF or RabLIF was added to the enriched basic medium, the efficiency of ES cell derivation increased to approximately 25% after 3 passages. The efficiency of ES cell derivation with either murine or rabbit LIF was comparable. The efficiency of ES cell derivation increased to approximately 50% when Rab9 conditioned medium was used in the absence of endogenous or added LIF. A similar ES cell derivation efficiency was obtained when basic medium was conditioned with the Rab9#19 cell line, which secreted endogenous Rab-LIF.

When blastocysts were cultured in basic medium conditioned on Rab9 or Rab9#19 fibroblast cells (FIGS. 3C and D), there was a facilitated outgrowth of inner cell mass cells. In enriched basic medium with added murine LIF or Rab-LIF, partial differentiation of the inner cell mass or outgrowth of throphectodermal cells was seen (cfr FIGS. 3A and B).

Already after one passage, a difference was observed in the morphology of ES cell colonies in different culture media. Enriched basic medium with added murine or Rab-LIF (FIGS. 4A and B) gave rise to rather flat ES colonies, while the use of basic medium conditioned on Rab9 or Rab9#19 fibroblast cells (FIGS. 4C and D) resulted in three-dimensional ES cell colonies. When basic medium was used all cells were differentiated after 1 passage (FIG. 4A). The results described above were preliminary results obtained after 3 weeks of culture. In a couple of instances, ES cells were obtained between 3 weeks and 2 months. The cumulative frequencies are summarised in table II.

TABLE II

Final efficiency of murine C57BL6/N ES cell derivation after 2 months of culture.

| Culture medium | Number of blastocysts explanted | Number of ES cell lines established | |
|---|---|---|---|
| | | Number | % |
| enriched basic medium | 21 | 0 | 0% |
| enriched basic medium with added murine LIF (1000 IU/ml) | 26 | 9 | 34% |
| enriched basic medium with added Rab-LIF (10 ng/ml) | 21 | 8 | 38% |
| enriched basic medium with added Rab-LIF (20 ng/ml) | 22 | 8 | 36% |
| basic medium conditioned on Rab9 fibroblast cells | 35 | 18 | 51% |
| basic medium conditioned on the Rab9 #19 fibroblast cell line | 18 | 11 | 61% |

In table II, only ES cell lines, which remained in an undifferentiated state during at least 10 passages, were considered as established ES cell lines.

When either murine LIF, 10 ng RabLIF or 20 ng RabLIF were added to the enriched basic medium, efficiency of ES cell derivation were 34%, 38% and 36% respectively. The efficiency of ES cell derivation with either murine or rabbit LIF was comparable. An ES cell derivation efficiency of 51% was obtained when Rab9 conditioned medium was used in the absence of endogenous or added LIF. An ES cell derivation efficiency of 61% was obtained when basic medium was conditioned with the Rab9#19 cell line, which secreted endogenous Rab-LIF. These differences (51% versus 61%) are not statistically significant (Chi Square analysis, P=NS).

5. Further Embodiment

In a second illustration of this invention, the blastocysts were obtained from the natural mating of FVB/NtacfBR (Taconic, Germantown, N.Y., USA) mice and from the natural mating of BALB/cAnNTacfBr (Taconic). The blastocysts were cultured with basic medium conditioned on Rab9 fibroblast cells according to example II.

The basic medium was composed of: 500 ml DMEM high glucose, 70 ml fetal bovine serum, 13 ml penicillin/streptomycin, 13 ml glutamine, 6.3 μl β-mercaptoethanol, and 13 ml non-essential amino acids. Enriched basic medium is basic medium to which another 4% (v:v) fetal bovine serum is added.

The basic medium conditioned by the Rab9 fibroblast cells is obtained as illustrated in Example II. To 1 liter of conditioned basic ES medium (from the mixture of the 4 collection days), 80 ml fetal bovine serum, 17 ml non-essential amino acids, 20 ml glutamine, 6.3 μl β-mercaptoethanol, 1.25 ml insulin and 80 ml basic medium is added and the pH adjusted to 7.4. This conditioned medium contains unmeasurable levels (less than 20 pg/ml) of Rab-LIF as determined with the ELISA for human LIF of R&D Systems (Minneapolis, Minn., USA), which fully cross-reacts with rabbit LIF.

TABLE III

Efficiency of ES cell derivation from FVB/N and Balb/C mice.

| Mouse strain | Number of blastcysts explanted | Number of ES cell lines established number | % |
|---|---|---|---|
| FVB/N | 20 | 8 | 40 |
| BALB/c | 34 | 15 | 44 |

The blastocysts are allowed to attach to the feeder layer. The culture medium is refreshed every day. After approximately 1 week in culture, the ICM outgrowth is removed from the trophectoderm and after trypsinization passed onto a new 96 well dish covered with a feeder layer of mitomycin C arrested murine fibroblasts. The ES cells are subsequently gradually passed onto larger culture dishes with a feeder layer. After 2 months of culture, the number of established ES cell lines is counted for each of the strains. The undifferentiated character of the established ES cell lines is determined by immunochemical staining for the presence of alkaline phosphatase (Vector Laboratories Inc., Burlingame, Calif.), or for the absence of vimentin and cytokeratin (both Dako A/S, Denmark). Only ES cell lines, which we were able to keep in culture in an undifferentiated state (more then 90% of undifferentiated cells) during at least 10 passages, were considered as established ES cell lines.

The basic medium conditioned by the Rab9 fibroblast cells allows the derivation of embryonic stem cells from the FVB/N as well as from the BALB/c strain. After two months of culture 8 established ES cell lines are counted for the FVB/N strain and 15 ES cell lines for the BALB/c strain. This implies an overall derivation efficiency of respectively 40% and 44%.

Example 4

Generation of Chimeric and ES Cell Derived Animals

The ability of the ES cells to colonize the germline of a host embryo can be tested by injection of these ES cells into host blastocysts, or by their aggregation with morula-stage diploid embryos or 4-celled tetraploid embryos, and implanting these chimeric preimplantation embryos into pseudopregnant foster recipients according to standard procedures. The resulting chimeric offspring can be test bred for germline transmission of the ES cell genome.

1. Blastocyst Injection of ES Cell Clones

The ability of the established ES cell lines from the C57BL/6, FVB/N and BALB/c mice to colonize the germline of a host embryo was tested by injection of these ES cell lines after 10 or more passages into host blastocysts and implantation of these chimeric embryos into pseudopregnant foster mothers using standard procedures. In order to allow easy estimation of the percentage chimerism (i.e. contribution of the ES cell genome to the chimeric offspring), ES cell lines from mouse strains with colored coats (C57BL/6N) were injected in Swiss Webster blastocysts, whereas ES cell lines from mice with white fur (BALB/c, FVB/N) were chimerized with black C57BL/6N blastocysts. Germline transmission of the ES cell genome was then tested by crossing high percentage chimeras with Swiss Webster or C57BL/6N mice, as appropriate, to establish the ES cell line derived coat color in F1 offspring.

Blastocyst injection was carried out using day 3.5 blastocysts collected from the uteri of superovulated females by flushing with M2 medium (Eurogentec, Seraing, Belgium). Superovulation was induced by injection of 7.5 I.U. of pregnant mare serum gonadotropin (PMSG, Sigma, St. Louis, Mo.) followed by injection of 7.5 I.U. of human chorionic gonadotropin (Pregnyl Organon, Oss, The Netherlands) after a 48 hour interval. The collected blastocysts were washed with and cultivated in M16 medium (Eurogentec) under 5% CO2 in air at 39° C.

ES cell lines were passaged two days before microinjection on bare gelatinized dishes. At the day of microinjection these dishes were trypsinized with 0.25% trypsin/1 mM EDTA (Invitrogen) for approximately 2 minutes at 39° C. The new conditioned cell culture medium was added and the suspension was pipetted to produce a single-cell suspension. After centrifugation (1100 rpm/min for 5 minutes) the ES cells were resuspended in the new conditioned cell culture medium and kept at 39° C. in the incubator.

Blastocyst injection was carried out by injecting 15-20 ES cells of mouse strains with colored coats (C57BL/6) into host blastocysts of albino Swiss Webster mice, or of ES cells of mice with a white coat (FVB/N, BALB/C) into host blastocysts of black C57BL/6N mice. After injection, blastocysts were reimplanted (7-8 blastocysts in each horn of the uterus) into 2.5 days pseudopregnant Swiss Webster females, previously mated to vasectomized males.

Eleven different C57BL/6N ES cell lines were injected into Swiss Webster blastocysts. Every C57BL/6N ES cell line was able to generate chimeric pups after blastocyst injection into blastocysts of Swiss Webster mice. All C57BL/6N ES cell lines have shown germline transmission after crossing high percentage chimeras with Swiss Webster mice and additional testing of the germline transmission capability is performed. Nine FVB/N and seven BALB/c ES cell lines were injected into C57BL/6N blastocysts. For each of these ES cell lines from the FVB/N strain as well as from the BALB/c strain chimeric pups were born after injection of into blastocysts of C57BL/6N mice. Seven FVB/N ES cell lines and five BALB/c ES cell lines have shown germline transmission capability. Additional testing of the germline transmission capability is performed.

TABLE IV

Production of chimeric mice after injection of Swiss Webster blastocysts with C57BL/6N ES cells, which were derived and cultured with basic medium conditioned on Rab9 fibroblasts.

| ES cell line No. | Passage No. | # blasts injected | # pups born | #chimeras | germline |
|---|---|---|---|---|---|
| C57BL/6N#3 | 11 | 48 | 10 | 5 | |
| C57BL/6N#39 | 10 | 37 | 11 | 6 | |
| C57BL/6N#29 | 17 | 36 | 4 | 4 | |
| C57BL/6N#6 | 15 | 24 | 2 | 1 | |
| C57BL/6N#29 | 22 | 26 | 5 | 5 | |
| C57BL/6N#6 | 19 | 34 | 8 | 8 | F1/1 |
| C57BL/6N#8 | 16 | 44 | 10 | 7 | |
| C57BL/6N#24 | 14 | 14 | 1 | 1 | |
| C57BL/6N#10 | 17 | 38 | 12 | 6 | |
| C57BL/6N#23 | 21 | 42 | 22 | 16 | F1/2 |
| C57BL/6N#3 | 15 | 32 | 9 | 5 | |
| C57BL/6N#11 | 17 | 61 | 14 | 9 | |
| C57BL/6N#9 | 10 | 29 | 8 | 3 | F1/1 |
| C57BL/6N#3 | 14 | 30 | 7 | 5 | M1/1 |
| C57BL/6N#10 | 19 | 31 | 8 | 4 | F1/3 M1/1 |
| C57BL/6N#19 | 12 | 31 | 4 | 2 | M2/2 |
| C57BL/6N#10 | 18 | 45 | 16 | 12 | F1/6 M1/3 |
| C57BL/6N#24 | 17 | 36 | 5 | 4 | M1/2 |
| C57BL/6N#11 | 18 | 45 | 11 | 6 | |
| C57BL/6N#3 | 18 | 53 | 8 | 4 | M1/1 |
| C57BL/6N#9 | 11 | 43 | 9 | 1 | |
| C57BL/6N#11 | 18 | 69 | 11 | 11 | F1/1 |
| C57BL/6N#11 | 19 | 31 | 8 | 1 | |
| C57BL/6N#29 | 25 | 32 | 14 | 4 | M2/2 F1/1 |
| C57BL/6N#3 | 19 | 54 | 10 | 3 | |
| C57BL/6N#9 | 15 | 27 | 3 | 2 | |
| C57BL/6N#29 | 28 | 43 | 17 | 7 | M2/2 |
| C57BL/6N#3 | 23 | 41 | 15 | 2 | M1/1 |
| C57BL/6N#11 | 22 | 13 | 6 | 1 | |
| C57BL/6N#9 | 18 | 42 | 12 | 1 | |
| C57BL/6N#29 | 30 | 49 | 11 | 1 | F0/1 |
| C57BL/6N#39 | 9 | 103 | 24 | 14 | M1/1 |
| C57BL/6N#24 | 15 | 31 | 9 | 6 | M1/1 F2/2 |
| C57BL/6N#39 | 12 | 14 | 7 | 3 | |
| C57BL/6N#19 | 13 | 56 | 20 | 7 | M2/2 F1/1 |
| C57BL/6N#24 | 14 | 13 | 5 | 5 | M1/2 |

M: germline transmission via male chimeras
F: germline transmission via female chimeras

TABLE Va

Production of chimeric mice after injection of C57BL/6 blastocysts with FVB/N ES cells, which were derived and cultured with basic medium conditioned on Rab9 fibroblasts.

| ES cell line No. | Passage No. | #blasts injected | #pups born | #chimeras | germline |
|---|---|---|---|---|---|
| FVB/N#7 | 10 | 16 | 7 | 4 | M2/2 |
| FVB/N#28 | 11 | 13 | 8 | 7 (mother died) | |
| FVB/N#11 | 11 | 30 | 6 | 6 | M3/3 |
| FVB/N#2 | 13 | 30 | 6 | 2 | M1/1 |
| FVB/N#23 | 14 | 34 | 7 | 4 | M2/3 |

TABLE Va-continued

Production of chimeric mice after injection of C57BL/6 blastocysts with FVB/N ES cells, which were derived and cultured with basic medium conditioned on Rab9 fibroblasts.

| ES cell line No. | Passage No. | #blasts injected | #pups born | #chimeras | germline |
|---|---|---|---|---|---|
| FVB/N#23 | 14 | 45 | 8 | 7 | M2/2 |
| FVB/N#3 | 16 | 18 | 3 | 0 | |
| FVB/N#18 | 18 | 16 | 5 | 3 | |
| FVB/N#35 | 15 | 70 | 3 | 3 | M1/1 |
| FVB/N#22 | 17 | 58 | 11 | 6 | M3/4 |
| FVB/N#7 | 14 | 47 | 21 | 14 | M4/4 |
| FVB/N#18 | 24 | 18 | 6 | 1 (died) | |

M: germline transmission via male chimeras
F: germline transmission via female chimeras

TABLE Vb

Production of chimeric mice after injection of C57BL/6N blastocysts with BALB/c ES cells, which were derived and cultured with basic medium conditioned on Rab9 fibroblasts.

| ES cell line No. | Passage No. | #blasts injected | #pups born | #chimeras | germline |
|---|---|---|---|---|---|
| BALB/c#12 | 10 | 30 | 3 | 1 | |
| BALB/c#9 | 11 | 53 | 8 | 5 | M2/2 |
| BALB/c#9 | 15 | 61 | 6 | 3 | |
| BALB/c#11 | 16 | 49 | 10 | 8 | M1/1 |
| BALB/c#4 | 16 | 36 | 3 | 2 | |
| BALB#12 | 18 | 64 | 10 | 9 | M0/2 F1/1 |
| BALB/c#4 | 20 | 14 | 12 | 7 | M1/1 |
| BALB/c#4 | 14 | 30 | 8 | 8 | M1/1 |
| BALB/c#11 | 22 | 15 | 6 | 5 | M2/2 |
| BALB/c18 | 12 | 24 | 8 | 3 | M1/1 |
| BALB/c#11 | 27 | 36 | 3 | 3 | |
| BALB/c#3 | 17 | 29 | 8 | 8 | |
| BALB/c#4 | 22 | 42 | 13 | 13 | M4/4 |
| BALB/c#18 | 18 | 16 | 3 | 1 | |
| BALB/c#18 | 20 | 29 | 8 | 1 | |
| BALB/c#25 | 28 | 14 | 4 | 4 | |
| BALB/c#3 | 24 | 17 | 3 | 1 | |

M: germline transmission via male chimeras
F: germline transmission via female chimeras 2. Diploid Aggregation of ES Cell Clones The diploid aggregation method can be executed as follows. Swiss Webster (albino coat colour) females are superovulated with pregnant mare serum gonadotropin followed 44-48 hrs later by 5 units human chorionic gonadotropin. The oviducts of superovulated and mated Swiss Webster mice are flushed 2.5 days after copulation to collect late 8-cell stage diploid embryos. All ES cell lines tested are derived from mice strains with a coat colour, facilitating identification of chimeric offspring.

Zonae pellucidae of these 8-cell stage diploid embryos are removed by treatment with acid Tyrode's buffer. The zona-free embryos are washed and placed in M16 medium. Aggregation is performed between one 8-cell stage diploid embryo and a clump of ES cells. The aggregates are cultured in micro drops of M16 until the blastocyst stage before they are reimplanted into the uterus horns of 2.5-day pseudopregnant Swiss Webster females.

Chimeric pups are identified by the presence of a dark (=non albino) colour, which originated from an ES cell contribution. The percentage of chimerism (portion of the newborn pup, originating from the ES cells) is visually identified by judging the percentage of dark coat (originating from the ES cells) compared to the white coat (originating from the albino Swiss Webster embryo).

3. Tetraploid Aggregation of ES Cell Clones

Completely ES cell derived embryos can be generated via aggregation of the ES cells with tetraploid host embryos. 2-celled embryos are electrically fused, and subsequently aggregated as 4-celled tetraploid embryos with the ES cells to form chimeric embryos, which are then implanted in pseudopregnant recipients. The ES cells (almost) exclusively contribute to the development of the embryo proper, and the tetraploid cells to that of the extra embryonic membrane.

In order to distinguish between the ES and tetraploid cells, host embryos (used for aggregation) are derived from the ROSA26 strain, which expresses LacZ ubiquitously and throughout the entire development and adulthood. The oviducts of superovulated and mated ROSA26 mice are flushed 36 hrs after treatment with human chorionic gonadotropin to collect late two-cell stage embryos.

Example 6

Ex vivo Expansion of Hematopoietic Stem Cells from Umbilical Cord Blood

1. Umbilical Cord Blood (UCB) Collection.

After informed consent, human UCB from full-term deliveries were collected at the Hospital Gasthuisberg (Leuven, Belgium) following the standard procedure used for UCB banking. The procedure consists of inserting the 16-gauge needle of a standard 450-ml blood donor set containing 35 ml of citrate-phosphate-dextrose-adenine (CPD-A) anticoagulant (Baxter Health Care, Deerfield, Ill.) into the umbilical vein of the delivered placenta and letting UCB drain by gravity into the blood bag. In all the case, blood samples were processed within 24 h after harvest. For each blood harvest, aliquots were set apart for routine haematological analysis (Cell-Dyn 3500 System, Abbott) and immunophenotyping of haematopoietic progenitors.

2. Isolation of Mononuclear Cells (MNC) and CD34+ Cell Purification.

Mononuclear cells (MNC) were isolated by diluting the buffy coat v/v in phosphate-buffered saline (PBS) (Gibco-BRL, Grand Island, N.Y.)) and layering 30 ml portions over 10 ml of Lymphoprep™ (Nycomed, Oslo, Norway). These samples were centrifugated at 2000 rpm for 20 min. The leukocyte-rich interface cells, now depleted of red blood cells were collected, washed and positively immunomagnetically enriched for CD34+ using the MACS CD34 Progenitor Cell Isolation Kit (Miltenyi Biotec, Auburn, Calif.) according to the manufacturer instructions. Briefly the MNC were washed and resuspended in Ca2+ free and Mg2+ free Dulbecco's PBS supplemented with 0.5% BSA (Fraction V, Sigma) and 2 mM EDTA. Cells were then incubated with an anti CD34 antibody coupled to MACS micro beads in the presence of a blocking reagent. Labeled cells were filtered through a 30 mm nylon mesh and then separated using a high gradient magnetic separation column placed in a strong magnetic field. Magnetically retained cells were eluted and their purity was determined by flow cytometry to be more than 95%.

3. Stroma Feeder.

The murine fetal liver cell line AFTO24 (a kind gift from Dr. Theunissen) was maintained at 33° C. in Dulbecco modified Eagle medium (DMEM, Gibco-BRL, Grand Island, N.Y.) supplemented with 20% FBS (HyClone, Logan, Utah), 100 U/ml penicillin, 100 U/ml streptomycine, 150 µM 2-mercaptoethanol (2-ME, Sigma Diagnostics, St Louis, Mo.). Cells were subcultured in 150 cm$^2$ Flasks and 6- or 96-well plates (Falcon, Becton Dickinson Labware, NJ) precoated with 0.1% gelatin (Speciality Media, Lavalette, N.J.); grown to confluency and moved at 37° C., 5% CO2 in order to stop the growth.

4. Culture of Hematopoietic Stem Cells.

Briefly, $10^5$ enriched UCB CD34+ cells were seeded in 6-well plates and cultured during 30 days:
1) on bare dish without stroma cells in medium conditioned by the rabbit fibroblast-like cell line Rab9 (ATCC CRL-1414)
2) on bare dish without stroma cells in medium conditioned by the rabbit fibroblast-like cell line Rab9#19 (Rab9#19 is the rabbit fibroblast cell line Rab9, stably transfected with the genomic rabbit LIF gene)
3) on bare dish without stroma cells in medium conditioned by the rabbit fibroblast-like cell line Rab9#19 (LMBP 5479CB)
4) on bare dish without stroma cells in enriched basic medium supplemented with insulin.
5) on bare dish without stroma cells in enriched basic medium supplemented with insulin.supplemented with 20 ng/ml human Flt3 ligand (rhFlt3/Flk2), 20 ng/ml human IL-6 recombinant (rhIL-6), 200 ng/ml human recombinant IL-6 Receptor soluble (rhIL-6 sR), 20 ng/ml human thrombopoietin (Tpo).

Cytokines (human Flt3 ligand (rhFlt3/Flk2), human IL-6 recombinant (rhIL-6), human recombinant IL-6 Receptor soluble (rhIL-6 sR), human thrombopoietin (Tpo) were obtained from R&D Systems, Minneapolis, Minn.

Twice a week, cells are fed with the fresh appropriate medium. Each 5 days until day 50, aliquots of cells were harvested for the performance of cell counts, phenotypic analysis, and in vitro assays (LTC-IC). The trypan blue exclusion method was used to determine the total viable cell content of expansion cultures. Originally $10^5$ enriched UCB CD34+ cells were seeded in 6-well plates and cultured during 30 days.

Figure 5:
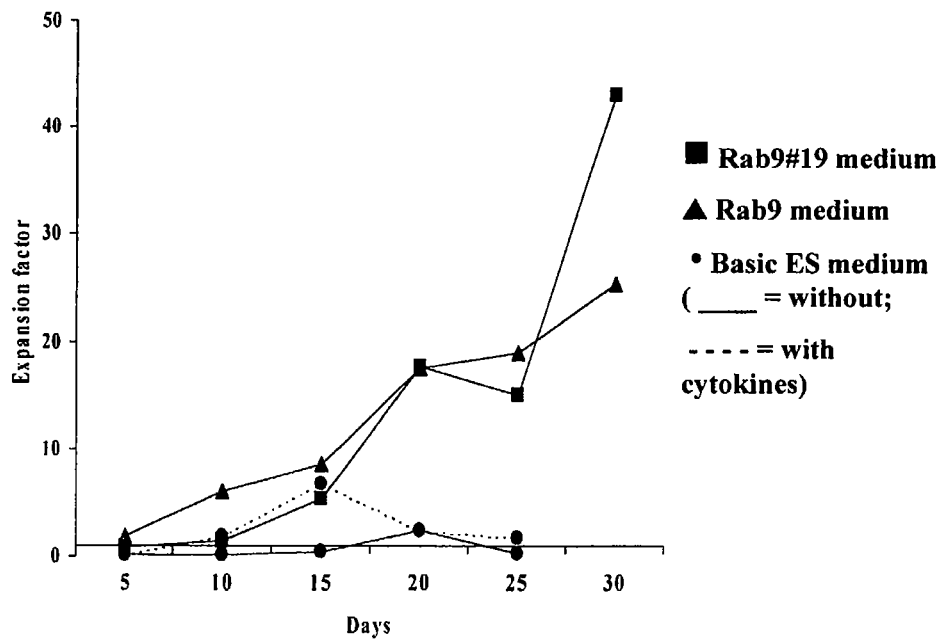
FIG. 5 shows the growth of expanded nucleated cells (depicted as expansion factor of the original population) of HUC derived CD34+ cells in different media. legend: full line with square: medium conditioned with Rab9#19 cells; full line with triangles: medium conditioned with Rab9 cells; full line with circle: basic ES medium; dotted line with circle: basic ES medium with added cytokines.

The results of the cell expansion are shown in table VI and FIG. 5. After 30 days the total cell number had increased 25 times when cultured in medium conditioned by Rab9 cells on bare dish without stroma cells. When cultured in medium conditioned by Rab9#19 cells on bare dish without stroma cells, an expansion factor of 43 was obtained.

CD34+ cells on bare dish without stroma cells in enriched basic medium supplemented with insulin with or without cytokine cocktail were all differentiated after 15 days of culture and all lost their hematopoietic cell phenotype.

TABLE VI

Expansion factor of nucleated cells cultured in different media. (Umbilical cord sample #40)

| Medium | Days in culture | | | | | |
|---|---|---|---|---|---|---|
| | 5 | 10 | 15 | 20 | 25 | 30 |
| Rab9#19 medium – cyt | 0.8 | 1.38 | 5.4 | 17.65 | 15 | 43 |
| Rab9 medium – cyt | 1.8 | 6.1 | 8.54 | 17.59 | 18.99 | 25.45 |
| Basic ES medium – cyt | 0.2 | 0.14 | 0.48 | 2.35 | 0.35 | — |
| Basic ES medium + cyt | 0.2 | 1.8 | 6.75 | 2.43 | 1.63 | — |

Table VI and FIG. 5 show that HSC and HSP grow significantly better in Rab9 or Rab9#19 conditioned cytokine free medium when compared with a basal medium which is used for isolation and maintenance of ES cells. The presence of LIF has a beneficial effect on the expansion of cells (compare Rab9 with Rab9#19).

5. Fluorescence-Activated Cell Sorting (FACS)

The CD34+ cells were first isolated as described above then labeled with a CD34-FITC-conjugated antibody (clone 581, Pharmingen, San Jose, Calif.) and a CD38-PE-conjugated antibody (clone HIT2, Pharmingen, San Jose, Calif.) for 15-20 min at room temperature. Then the cells were washed twice with PBS, and then analysed on a FACSCalibur flow cytometer (Becton Dickinson, San Jose, Calif.) equipped with a 488 nm argon laser. Isotype matched controls conjugated with FITC and PE were used to set the analyzing gates. During culture samples were taken at 5 days intervals to count the number of $CD34^+$ cells and $CD34^+CD38^-$ cells.

Figure 6:
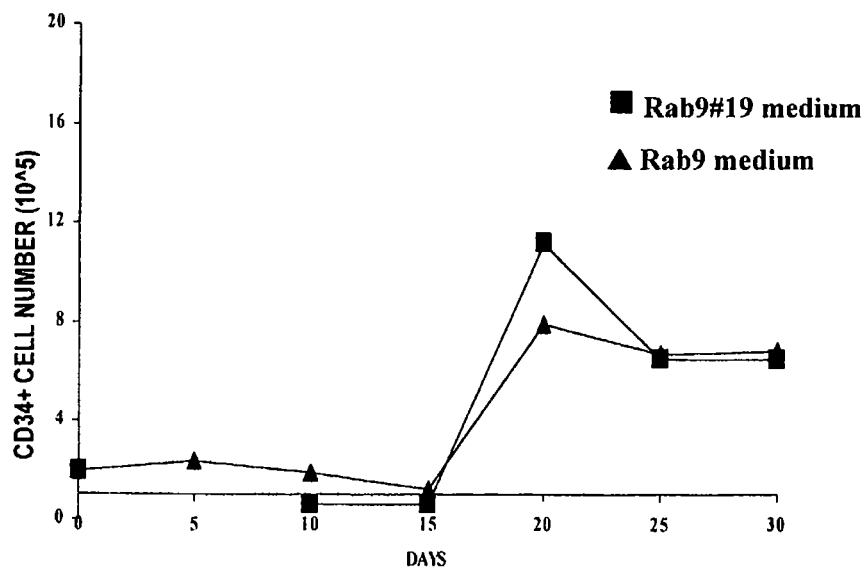
FIG. 6: Expansion of CD 34+ positive cells (depicted as expansion factor of the original CD34+ positive cells) in cultures of HUC derived CD34positive cells in different media. legend: full line with squares: medium conditioned with Rab9#19 cells; full line with triangles: medium conditioned with Rab9 cells.

Table VII and FIG. 6 show that after 30 days of cultivation, the number of $CD34^+$ cells had increased about 3 times in medium conditioned by Rab9 cells on bare dish without stroma cells. A similar increase was observed when the cells were cultured in medium conditioned by Rab9#19 cells on bare dish without stroma cells.

The number of CD34+ and CD34+CD38− cells on bare dish without stroma cells in enriched basic medium supplemented with insulin in the presence or absence of the cytokines cocktail could not be counted due to their extremely weak capacity of expansion. There were not enough cells available for a flow cytometry analysis.

TABLE VII

Number of $CD34^+$ cells ($\times 10^5$ cells) during 30 days of culture. (Umbilical cord sample #40) bd: below detection limit, not enough cells available for performing cell.

| Medium | Days in culture | | | | | | |
|---|---|---|---|---|---|---|---|
| | 0 | 5 | 10 | 15 | 20 | 25 | 30 |
| Rab9#19 medium | 1.98 | — | 0.61 | 0.64 | 11.18 | 6.47 | 6.47 |
| Rab9 medium | 1.98 | 2.42 | 1.94 | 1.24 | 7.94 | 6.69 | 6.84 |
| basic ES medium + Insulin | bd | bd | bd | bd | bd | bd | bd |
| basic ES medium + insulin + added cytokines | bd | bd | bd | bd | bd | bd | bd |

6. LTC-IC Assays.

The most frequently used method for assessing the frequency of primitive cells in vitro is the long-term culture initiating cell (LTC-IC) assay. The LTC-IC forms foci or "cobblestone areas" of primitive hematopoietic cells in the stroma. These areas quantify by limiting dilution assays the primitive progenitors that generate mostly myeloid cells after 5 weeks in culture on a hematopoietic supportive stroma. LTC-IC has been found in the CD34+ fraction with a heterogeneous expression of CD38. These assays do not measure self-renewal, multilineage potential, or engraftment potential of progenitors (de Wynter E., Ploemacher R. E. (2001) in J. Biol. Regul. Homeost. Agents, 15: 23-7).

CD34+ cells from expansion cultures were plated in 6 limiting dilutions of 11 replicates on AFTO24-coated 96-well plates. Medium consisted of Iscoves modified Dulbecco medium (IMDM) supplemented with 12.5% FBS, 12.5% horse serum (Stem Cell Technologies, Vancouver, Canada), 1000 U/ml penicillin, 1000 U/ml streptomycin, 2 micromol L-Glutamine (Gibco-BRL) and $10^{-6}$ micromol hydrocortisone. Cultures were maintained for 5 weeks with half-medium change weekly. Medium was then completely removed and replaced with clonogenic methycellulose medium (MethoCult™ GF H4434, Stem Cell technologies) consisting of 1.12% methylcellulose, IMDM, 30% FBS, 3 U/ml erythropoietin, 50 ng/ml rh Stem Cell Factor, 10 ng/ml rh GM-CSF, 10 ng/ml rh IL-3, $10^{-4}$ M 2-mercaptoethanol After 2 weeks culture in this methylcellulose medium, wells were evaluated for the presence or absence of hematopoietic colonies and scored as positive or negative respectively. LTC-IC frequency was then calculated according to Poisson statistics.

After 15 days of culture the number of LTC-IC had increased 18 times when cultured in medium conditioned by Rab9 cells on bare dish without stroma cells and without the addition of cytokines. When cultured in medium conditioned by Rab9#19 cells on bare dish without stroma cells and without the addition of cytokines, an expansion factor of only 3.8 was obtained. The absence of LIF in the conditioned medium has a beneficial effect on the expansion of long LTC-IC.

The LTC-IC for cultures on bare dish without stroma cells in enriched basic medium supplemented with insulin and with or not cytokines cocktail was not analyzed due to availability of enough cells under these culture conditions.

TABLE VIII

Expansion factor of LTC-IC. (Umbilical cord sample #23)

| Medium | Days in culture | | |
|---|---|---|---|
| | 5 | 10 | 15 |
| Rab9#19 medium | 0.95 | 0.81 | 3.85 |
| Rab9 medium | 2.2 | 12 | 18.4 |
| basic ES medium + insulin | * | * | * |
| basic ES medium + insulin + cyt | * | * | * |

*: too few cells available due to limited growth.

Figure 7:
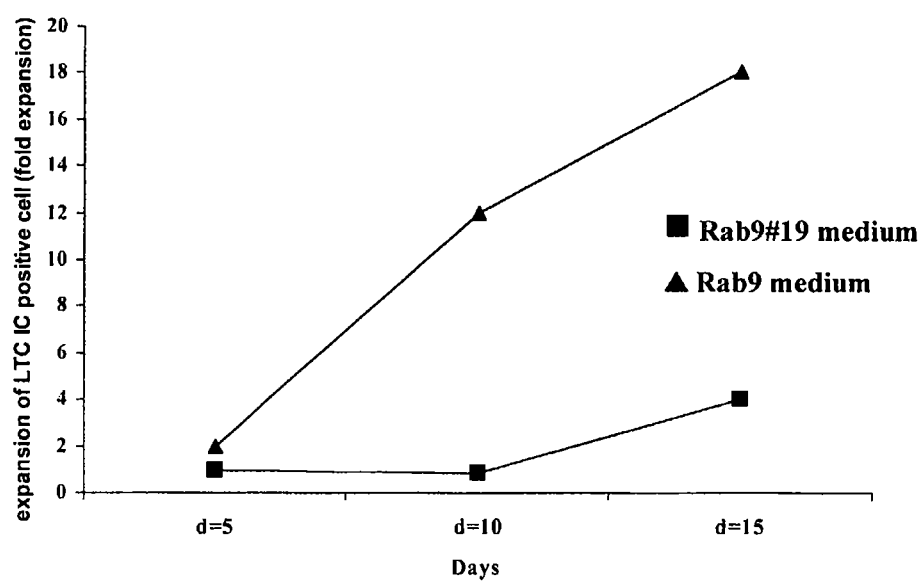
FIG. 7: Expansion of LTC-IC positive cells (depicted as expansion factor of the original LTC-IC positive cells) in cultures of HUC derived CD34 positive cells in different media. legend: full line with squares: medium conditioned with Rab9#19 cells; full line with triangles: medium conditioned with Rab9 cells.

The results presented in table VIII and FIG. 7 clearly show the influence of LIF on the differentiation capacity of the expanded cells. The absence of LIF in the Rab9 medium dramatically preserve the potential of the cells to differentiate in the myeloid lineage. The results also show that the novel Rab9 medium, which has superior capacities for deriving and maintaining ES cells, also has a superior performance in promoting the growth and maintaining the undifferentiated status of hematopoeitic stem cells and stem cell precursors.

Example 8

In vivo Assay for Repopulating HSC

Properties of HSC are self-renewal, multilineage differentiation capacity, and ability to repopulate a myeloablated host. Assays such as the long-term culture-initiating cell (LTC-IC) measure the ability of cells to generate myeloid progenitors after a prolonged period in culture. However, these assays do not measure self-renewal, multilineage potential, or engraftment potential of progenitors. Assessment of the engrafting ability of human HSC requires still requires transplant models. Several xenogeneic models have been developed, including transplantation transplantation into the humanized severe combined immunodeficiency (SCID) mouse into nonobese diabetic (NOD)-SCID mice the Beige-Nude-Xid (BNX) mouse and preimmune fetal sheep as describe for example in Lewis et al (2001) Blood 97, 3441-3449

NOD-SCID Recipients. A breeding colony of NOD-SCID mice was Mice were kept in specific pathogen-free conditions and maintained on acidified water and autoclaved food. Trimethoprim 60 mg and sulfamethoxazole 300 mg (Hoffmann- La Roche, Nutley, N.J.) per 100 mL water was given twice weekly. At 6 to 8 weeks of age, mice were irradiated with 300 to 325 cGy at 57 cGy/min by a Mark 1 Cesium irradiator. Transplantation of UCB cells by tail vein injection occurred 24 hours after irradiation. Cell doses ranged from 25 to 150× $10^3$ $^{CD}$341 cells on day 0 (ie, uncultured) or the progeny of an identical number of cultured cells on days 7, 14, or 28. Six weeks after transplantation, mice were killed by cervical dislocation. Bone marrow (BM) was obtained by flushing femurs and tibias with IMDM 20% FCS. Cells from engrafted animals were then used for either secondary transplant experiments or extended phenotypes. When more than 2% human CD451 cells were present in the murine marrow, cells from 2 femurs and 2 tibias were transplanted into individual secondary mouse recipients. Assessment of donor cell engraftment was by detection of the humanspecific pan-leukocyte antigen CD45 (Becton Dickinson Immunocytometry Systems, San Jose, Calif.) conjugated to fluorescein isothiocyanate (FITC) or peridinin chlorophyll (PerCP). Three-color phenotyping was performed by staining cells with antihuman CD45 PerCP (Becton Dickinson), antimouse CD45 FITC (Pharmingen, San Diego, Calif.), and antihuman CD3 phycoerythrin (PE), CD14 PE, CD19 PE, CD33 PE, or CD34 PE (all from Becton Dickinson). Appropriate isotype controls were used. The frequency of the engrafting human cell in the mouse, defined as an SRC, was calculated by limiting dilution analysis. Mice were infused with increasing cell numbers and engraftment defined as detection of more than 0.5% human CD451 cells. SRC frequency was calculated by Poisson statistics Fetal Sheep Recipients. Cultured cells were suspended Rab9 conditioned medium. Fifty (group X) to 100 (group I) 3 $10^3$ uncultured CD341 cells or the progeny of an identical number of cells cultured for 7 (group XI and II) or 14 (group XII and III) days were injected into preimmune (day 57-62 of gestation) fetal sheep recipients using the amniotic bubble procedure. In some experiments, animals were killed 60 days after transplantation and BM analyzed for human cells. The BM also served as the source of CD451 cells for transplant into secondary recipients.

Alternatively, animals were allowed to be born and BM examined 6 months after transplantation. For secondary transplants, human CD451 cells were isolated from the BM of primary recipients from groups I, II, and III at 60 days after transplant by panning. The CD451 cells from the 2 animals from each group were pooled, analyzed for CD341 cell content, and injected into 3 secondary fetal recipients (group I, group IV, group II, group V, group III, group VI).

Animals were killed on day 60 after transplantation and the BM cells were analyzed for the presence of human cells. Marrow of these secondary recipients served as the source of CD451 cells transplanted into tertiary recipients. All recipients were killed on day 60 after transplantation and the BM cells were analyzed for the presence of human cells. For assessment of donor cell engraftment, BM MNC from the fetal and newborn sheep transplanted with human cells were analyzed for the presence of human cells by flow cytometry. Briefly, MNC were isolated from BM by hypotonic lysis of contaminating red cells. Antibodies specific for human CD3, CD20, CD33, CD34, CD45, and glycophorin A (Becton Dickinson) were conjugated to either FITC or PE. In each sample, 5-3 $10^5$ cells were labeled and expression of each antigen compared to the appropriate non-binding isotype-matched control. Expression levels of 0.2% or more could be detected. In addition, BM MNC were cultured in methylcellulose (0.4-2 3 $10^5$ cells/mL) with supplemental erythropoietin (2 IU/mL), IL-3 (5 ng/mL), and GM-CSF (5 ng/mL) and human CFU-GM and CFU-Mix enumerated.

These in vivo assays are proof for the long term engrafting capacity of HSC as cultivated in the novel compositions of the present invention.

What is claimed is:

1. A method of establishing pluripotent embryonic stem cells from mouse blastocysts, or of maintaining or growing established pluripotent embryonic stem cells from a mouse blastocyst for at least 10 passages as undifferentiated cells, or of maintaining or growing human umbilical cord blood (UCB) CD 34+ cells, said method comprising the step of cultivating said stem cells or precursor cells for at least one passage in basal embryonic stem cell medium preconditioned by the rabbit fibroblast cell line Rab9 (ATCC catalogue CRL1414) and containing less than 0.1 ng/ml Leukemia Inhibitory Factor (LIF).

2. The method according to claim 1, wherein said preconditioned medium is supplemented with one or more compounds of the group selected from interleukin, oncostatin, ciliary neurotrophic factor, stem cell factor, basic fibroblast growth factor, and cardiotrophin.

3. The method according to claim 1, wherein said preconditioned medium is supplemented with newborn serum or adult serum.

4. The method according to claim 1, wherein said preconditioned medium contains less than 0.05 ng/ml Leukemia Inhibitory Factor (LIF).

5. The method according to claim 1, wherein said preconditioned medium contains less than 20 pg/ml Leukemia Inhibitory Factor (LIF).

6. The method according to claim 1, wherein said mouse stem cells are stem cells of a *Mus musculus* strain with a genetic background selected from the group consisting of 129/SvEv, C57BL/6N, C57BL/6J-HPRT, BALB/cAnN, CBA/CaOla, 129/SvJ, DBA/2N, DBA/1CaOla, C3H/HeN, C57BL/6Ola, FVB/N and Swiss Webster.

7. The method according to claim 1, which comprises cultivating the human umbilical cord blood (UCB) CD34+ cells until an expansion by at least 25 fold is obtained or until the amount of nucleated cells are being expanded by at least 10 fold.

8. The method according to claim 1 wherein said basal embryonic stem cell medium consists of Dulbecco's Modified Eagle Medium (DMEM), non-essential amino acids, glutamine, β-mercaptoethanol and fetal bovine serum.

9. The method according to claim 1 wherein said preconditioned medium comprises per liter of conditioned medium an added volume of 50 to 120 ml of fetal bovine serum, 10 to 25 ml non-essential amino acids, 2 to 8 μl β-mercaptoethanol, 0.5 to 2.5 ml insulin, and 80 to 130 ml basal embryonic stem cell medium.

10. The method according to claim 1 wherein said UCB CD34+ cells are enriched UCB CD34+ cells.

11. A method for deriving and culturing pluripotent murine embryonic stem cells, said method comprising the steps of:
   i) isolating inner mass cells from murine blastocyst stage embryos
   ii) culturing inner mass cells isolated from the blastocysts
   iii) passaging the inner mass cells periodically
   wherein said culturing and passaging is in a composition comprising basal embryonic stem cell medium preconditioned by the rabbit fibroblast cell line Rab9 (ATCC catalogue CRL1414) and containing less than 0.1 ng/ml Leukemia Inhibitory Factor (LIF).

12. The method according to claim 11 wherein the inner mass cells are passaged for at least 8 times.

* * * * *

UNITED STATES PATENT AND TRADEMARK OFFICE
CERTIFICATE OF CORRECTION

PATENT NO. : 8,993,323 B2
APPLICATION NO. : 14/031592
DATED : March 31, 2015
INVENTOR(S) : Luc Schoonjans It is certified that error appears in the above-identified patent and that said Letters Patent is hereby corrected as shown below:

In The Claims

Column 33, Line 53, Claim 6, replace "CBA/CaOIa, 129/SvJ, DBA/2N, DBA/1CaOIa," with --CBA/CaOla, 129/SvJ, DBA/2N, DBA/1CaOla,--;

Line 54, replace "C57BL/6OIa," with --C57BL/6Ola,--.

Signed and Sealed this
Twenty-second Day of September, 2015

Michelle K. Lee
*Director of the United States Patent and Trademark Office*